US008293245B2

(12) United States Patent
Smith et al.

(10) Patent No.: US 8,293,245 B2

(45) Date of Patent: Oct. 23, 2012

(54) METHODS AND COMPOSITIONS BASED ON SHIGA TOXIN TYPE 1 PROTEIN

(75) Inventors: Michael Smith, Silver Spring, MD (US); Angela Melton-Celsa, Sterling, VA (US); Alison O'Brien, Bethesda, MD (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 225 days.

(21) Appl. No.: 11/788,546

(22) Filed: Apr. 20, 2007

(65) Prior Publication Data

US 2007/0292426 A1 Dec. 20, 2007

Related U.S. Application Data

(60) Provisional application No. 60/793,918, filed on Apr. 20, 2006.

(51) Int. Cl.
*A61K 39/00* (2006.01)

(52) U.S. Cl. ...................... 424/192.1; 530/300; 530/350

(58) Field of Classification Search ........................ None
See application file for complete search history.

(56) References Cited

U.S. PATENT DOCUMENTS

| | | | |
|---|---|---|---|
| 5,164,298 | A | 11/1992 | Lingwood et al. |
| 5,747,272 | A | 5/1998 | O'Brien et al. |
| 5,866,692 | A | 2/1999 | Shitara et al. |
| 5,968,894 | A | 10/1999 | Lingwood et al. |
| 7,910,095 | B2 | 3/2011 | Tzipori et al. |
| 7,910,096 | B2 | 3/2011 | Tzipori et al. |
| 7,910,706 | B2 | 3/2011 | Tzipori et al. |
| 2002/0160005 | A1 | 10/2002 | Tzipori et al. |
| 2003/0082189 | A1 | 5/2003 | Tzipori et al. |
| 2003/0170248 | A1 | 9/2003 | Stinson et al. |
| 2005/0226883 | A1 | 10/2005 | Averback et al. |
| 2007/0292426 | A1 | 12/2007 | Smith et al. |
| 2008/0063598 | A1 | 3/2008 | Averback et al. |
| 2008/0107653 | A1 | 5/2008 | Vermeij |
| 2009/0226469 | A1 | 9/2009 | Smith et al. |
| 2009/0258010 | A1 | 10/2009 | Riviere et al. |

FOREIGN PATENT DOCUMENTS

| | | | | |
|---|---|---|---|---|
| EP | 0 239 400 | | | 9/1987 |
| EP | 0 239 400 | A2 | | 9/1987 |
| JP | 62-292890 | | | 12/1987 |
| WO | WO 94/04679 | | | 3/1994 |
| WO | WO 98/11229 | | * | 3/1998 |
| WO | WO 98/20903 | | | 5/1998 |
| WO | WO 99/32645 | | | 7/1999 |
| WO | WO 99/45962 | | | 9/1999 |
| WO | WO 99/59629 | | | 11/1999 |
| WO | WO 2005/052158 | A1 | | 6/2005 |
| WO | WO 2005/075647 | | | 8/2005 |
| WO | WO 2007/098201 | | | 8/2007 |
| WO | WO 2007/124133 | | | 11/2007 |
| WO | WO 2008/080218 | A1 | | 7/2008 |
| WO | WO 2010/085539 | | | 7/2010 |

OTHER PUBLICATIONS

Boyd et al (Infection and Immunity, Mar. 1991, p. 750-757).*

Cox et al (Vaccine, Vo. 15, No. 3, pp. 248-256, 1997).*

Bose et al., "High Affinity Mouse-Human Chimeric Fab Against Hepatitis B Surface Antigen," *World J. Gastroenterol.* 11:7569-7578 (2005).

Boyd et al., "Serological Responses to the B Subunit Shiga-Like Toxin 1 and Its Peptide Fragments Indicate that the B Subunit is a Vaccine Candidate to Counter the Action of the Toxin," *Infect. Immun.* 59(3):750-757 (1991).

Bowie et al., "Deciphering the Message in Protein Sequences: Tolerance to Amino Acid Substitutions," *Science* 247:1306-1310 (1990).

Campbell, "Monoclonal Antibody Technology," *Laboratory Techniques in Biochemistry and Molecular Biology*. Elsevier Science Publishers B.V. vol. 13:186-187 (1984).

"Clinical Roundup," *Bioworld Today* 19(61) (2008).

Cox et al., "Adjuvants—A Classification and Review of Their Modes of Action," *Vaccine* 15:248-256 (1997).

Dowling et al., "Phase 1 Safety and Pharmacokinetic Study of Chimeric Murine-Human Monoclonal Antibody cαStx2 Administered Intravenously to Healthy Adult Volunteers," *Antimicrob. Agents Chemother.* 49(5):1808-1812 (2005).

Downes et al., "Affinity Purification and Characterization of Shiga-Like Toxin II and Production of Toxin-Specific Monoclonal Antibodies," *Infection and Immunity* 56:1926-1933 (1988).

Edwards et al., "Humanization of Monoclonal Antibodies Against *Escherichia colo* Toxins STX1 and STX2," In *VTEC '97: 3rd International Symposium and Workshop on Shiga Toxin* (*Verocytotoxin*)-*Producing Escherichia coli Infections* V110/V11:113 (1997) (Abstract).

Edwards et al., "Vero Cell Neutralization and Mouse Protective Efficacy of Humanized Monoclonal Antibodies Against *Escherichia coli* Toxins Stx1 and Stx2," *Escherichia coli O157:H7 and Other Shiga Toxin-Producing E. coli Strains* J. Kaper and A. O'Brien, Editors 388-392 (1998).

Greenspan and Di Cera, "Defining Epitopes: It's Not as Easy as it Seems," *Nat. Biotechnol.* 17:936-937 (1999).

Islam and Stimson, "Production and Characterization of Monoclonal Antibodies with Therapeutic Potential Against Shiga Toxin," *J. Clin. Lab Immunol.* 33:11-16 (1990).

(Continued)

*Primary Examiner* — Patricia A Duffy

(74) *Attorney, Agent, or Firm* — Clark & Elbing LLP

(57) ABSTRACT

The invention is based on the discovery of the epitope in the Stx1 protein for the 13C4 antibody. The invention features non-full length Stx1 polypeptides that include the epitope for the 13C4 monoclonal antibody epitope. The invention also features methods of producing anti-Stx1 antibodies specific for the 13C4 epitope of the Stx1 protein. Additionally, the invention features methods for treating a subject having, or at risk of developing, a Shiga toxin associated disease (e.g., hemolytic uremia syndrome and diseases associated with *E. coli* and *S. dysenteriae* infection) with a polypeptide that includes the 13C4 epitope or with an anti-Stx1 antibody developed using the methods of the invention. Furthermore, the invention features the detection of Stx1 in a sample using the antibodies developed using the methods of the invention.

23 Claims, 11 Drawing Sheets

OTHER PUBLICATIONS

Jackson et al., "Functional Analysis of the Shiga Toxin and Shiga-Like Toxin Type II Variant Binding Subunits by Using Site-Directed Mutagenesis," *J. Bacteriol.* 172:653-658 (1990).

Kelley, "Engineering Therapeutic Antibodies," *Protein Engineering: Principles and Practice* J.L. Cleland and C.S. Craik, Editors Chapter 15:399-434 (1996).

LaCasse et al., "Shiga-Like Toxin-1 Receptor on Human Breast Cancer, Lymphoma, and Myeloma and Absence From CD34$^{30}$ Hematopoietic Stem Cells: Implications for Ex Vivo Tumor Purging and Autologous Stem Cell Transplantation," *Blood* 94(8):2901-2910 (1999).

LoBuglio et al., "Mouse/Human Chimeric Monoclonal Antibody in Man: Kinetics and Immune Response," *Proc. Natl. Acad. Sci. U.S.A.* 86:4220-4224 (1989).

Ma et al., "Engineering an Anti-Stx2 Antibody to Control Severe Infections of EHEC O157:H7," Immunol. Lett. 121(2):110-115 (2008).

Morrison, "With FDA Talks Stalled, Thallion Looks Abroad," *Bio World Today* 18(211):1-7 (2007).

O'Brien and Laveck, "Immunochemical and Cytotoxic Activities of *Shigella dysenteriae* 1 (Shiga) and Shiga-Like Toxins," *Infect. Immun.* 35:1151-1154 (1982).

Paton and Paton, "Pathogenesis and Diagnosis of Shiga Toxin-Producing *Escherichia Coli* Infections," *Clin. Microbiol. Rev.* 11:450-479 (1998).

Perera et al. "Isolation and Characterization of Monoclonal Antibodies to Shiga-Like Toxin II of Enterohemorrhagic *Escherichia coli* and Use of the Monoclonal Antibodies in a Colony Enzyme-Linked Immunosorbent Assay," *J. Clin. Microbiol.* 26:2127-2131 (1988).

Rüssmann et al., "Variants of Shiga-like toxin II Constitute a Major Toxin Component in *Escherichia coli* 0157 Strains From Patients With Haemolytic Uraemic Syndrome," *J.Med. Microbiol.* 40:338-343 (1994).

Schmitt et al., "Two Copies of Shiga-Like Toxin II-Related Genes Common in Enterohemorrhagic *Escherichia coli* Strains Are Responsible for the Antigenic Heterogeneity of the O157:H— Strain E32511," *Infect. Immun.* 59:1065-1073 (1991).

Simon et al., "Shiga Toxin 1 Elicits Diverse Biologic Responses in Mesangial Cells," *Kidney Int* 54:1117-1127 (1998).

Smith et al., "Development of a Hybrid Shiga Holotoxoid Vaccine to Elicit Heterologous Protection Against Shiga Toxins Types 1 and 2," *Vaccine* 24:4122-4129 (2006).

Smith et al., "The 13C4 Monoclonal Antibody that Neutralizes Shiga Toxin Type 1 (Stx1) Recognizes Three Regions on the Stx1 B Subunit and Prevents Stx1 From Binding to Its Eukaryotic Receptor Globotriaosylcermide," *Infect. Immun.* 74(12):6992-6998 (2006).

Smith, et al., "Epitope Mapping of Monoclonal Antibodies 13c4 and 11e10 that Neutralize Stx1 and Stx2, Respectively" (Abstract), presented at the Vero toxin-producing *Escherichia coli* (VTEC) meeting in Edinburgh, Scotland, Jun. 8-12, 2003.

Smith, et al., "The 13C4 Monoclonal Antibody that Neutralizes Shiga Toxin (Stx) Type 1 Binds to Three Regions on the Stx1 B Subunit," (Abstract), presented at the American Society for Microbiology General Meeting held in Orlando, Florida, May 21-25, 2006, and published in ISBN 1-555813887.

Speirs and Akhtar, "Detection of *Escherichia Coli* Cytotoxins by Enzyme-Linked Immunosorbent Assays," *Can. J. Microbiol.* 37:650-653 (1991).

Strockbine et al., "Characterization of Monoclonal Antibodies Against Shiga-Like Toxin From *Escherichia coli," Infect. Immun.* 50:695-700 (1985).

Tesh et al., "Comparison of the Relative Toxicities of Shiga-Like Toxins Type I and Type II for Mice," *Infect. Immun.* 61:3392-3402 (1993).

Wen et al., "Genetic Toxoids of Shiga Toxin Types 1 and 2 Protect Mice Against Homologous But Not Heterologous Toxin Challenge," *Vaccine* 24:1142-1148 (2006).

International Preliminary Report on Patentability issued Oct. 22, 2008 (PCT/US07/09799).

International Search Report mailed Sep. 26, 2008 (PCT/US07/09799).

Written Opinion of the International Searching Authority mailed Sep. 26, 2008 (PCT/US07/09799).

Requirement for Restriction/ Election (U.S. Appl. No. 09/215,163) mailed Feb. 14, 2000.

Reply to Restriction Requirement (U.S. Appl. No. 09/215,163) filed Mar. 14, 2000.

Non-Final Office Action (U.S. Appl. No. 09/215,163) mailed Jun. 6, 2000.

Reply to Non-Final Office Action (U.S. Appl. No. 09/215,163) filed on Oct. 5, 2000.

Non-Final Office Action (U.S. Appl. No. 09/215,163) mailed Dec. 14, 2000.

Reply to Non-Final Office Action (U.S. Appl. No. 09/215,163) filed on Mar. 14, 2001.

Final Office Action for U.S. application (U.S. Appl. No. 09/215,163) mailed May 23, 2001.

Reply to Final Office Action (U.S. Appl. No. 09/215,163) filed on Nov. 21, 2001.

Advisory Action (U.S. Appl. No. 09/215,163) mailed Feb. 27, 2002.

Continued Prosecution Application (U.S. Appl. No. 09/215,163) filed on Jun. 21, 2002.

Non-Final Office Action (U.S. Appl. No. 09/215,163) mailed Sep. 10, 2002.

Reply to Non-Final Office Action (U.S. Appl. No. 09/215,163) filed on Feb. 10, 2003.

Final Office Action (U.S. Appl. No. 09/215,163) mailed Sep. 22, 2003.

Reply to Final Office Action (U.S. Appl. No. 09/215,163) filed on Mar. 22, 2004.

Advisory Action (U.S. Appl. No. 09/215,163) mailed May 17, 2004.

Reply to Non-Final Office Action and Request for Continued Examination (U.S. Appl. No. 09/215,163) filed on Oct. 22, 2004.

Non-Final Office Action (U.S. Appl. No. 09/215,163) mailed Nov. 30, 2006.

Reply to Non-Final Office Action (U.S. Appl. No. 09/215,163) filed on May 30, 2007.

Final Office Action (U.S. Appl. No. 09/215,163) mailed Sep. 25, 2007.

Reply to Final Office Action and Request for Continued Examination (U.S. Appl. No. 09/215,163) filed on Oct. 30, 2007.

Non-Final Office Action (U.S. Appl. No. 09/215,163) mailed Feb. 13, 2008.

Requirement for Restriction/ Election (U.S. Appl. No. 11/471,369) mailed Jun. 23, 2008.

Reply to Restriction Requirement (U.S. Appl. No. 11/471,369) filed on Oct. 23, 2008.

Requirement for Restriction/ Election (U.S. Appl. No. 11/471,420) mailed Jun. 23, 2008.

Reply to Restriction Requirement (U.S. Appl. No. 11/471,420) filed Oct. 23, 2008.

Stinson et al., *PCR Strategies: Generation of single-chain antibody fragments by PCR*. California: Academic Press, Inc., 1995.

Office Action for U.S. Appl. No. 11/471,369 mailed on Feb. 6, 2009.

Office Action for U.S. Appl. No. 11/471,420 mailed Feb. 6, 2009.

Office Action for U.S. Appl. No. 09/215,163 mailed Jun. 29, 2009.

Canada Communicable Disease Report, "Investigation of an *E. coli* O157:H7 Outbreak in Brooks, Alberta, Jun.-Jul. 2002: The Role of Occult Cases in the Spread of Infection Within a Daycare Setting," 29-03:1-6 (2003).

Fagerberg et al., "Tumor Regression in Monoclonal Antibody-Treated Patients Correlates with the Presence of Anti-Idiotype-Reactive T Lymphocytes," *Cancer Research* 55:1824-1827 (1995).

Gouveia et al., "Genomic Comparisons and Shiga Toxin Production Among *Escherichia coli* O157:H7 Isolates from a Day Care Center Outbreak and Sporadic Cases in Southeastern Wisconsin," *J. Clin. Microbiol.* 36:727-733 (1998).

Lakewood-Amedex Press Release dated Jan. 17, 2011.

Lindgren et al., "Virulence of Enterohemorrhagic *Escherichia coli* O91:H21 Clinical Isolates in an Orally Infected Mouse Model," *Infection and Immunology* 61:3832-3842 (1993).

Marques et al., "*Escherichia coli* Strains Isolated from Pigs with Edema Disease Produce a Variant of Shiga-Like Toxin II," *FEMS Lett.* 44:33-38 (1987).

Miliwebsky et al., "Prolonged Fecal Shedding of Shiga Toxin-Producing *Escherichia coli* Among Children Attending Day-Care Centers in Argentina," *Revista Argentina de Microbiologia* 39:90-92 (2007).
O'Brien and Holmes, "Shiga and Shiga-Like Toxins," *Microbiol. Rev.* 51:206-220 (1987).
O'Donnell et al., "Outbreak of Vero Cytotoxing-Producing *Escherichia coli* O0157 in a Child Day Care Facility," *Commun. Dis. Public. Health* 5:54-58 (2002) (Abstract).
Sheoran et al., "Stx2-Specific Human Monoclonal Antibodies Protect Mice Against Lethal Infection with *Escherichia coli* Expressing Stx2 Variants," *Infect. Immun.* 71:3125-3130 (2003).
Stinson et al., *PCR Strategies: Generation of Single-Chain Antibody Fragments by PCR*. California: Academic Press, Inc., pp. 300-312 (1995).
Japanese Notice of Reasons of Rejection for Application No. 2000-525563, dated Oct. 31, 2008 (English Translation).
European Official Communication for EP 98965434.8, dated Aug. 9, 2007.
Reply to European Official Communication for EP 07795522.7, dated Oct. 25, 2010.
International Search Report (PCT/US10/21610), dated Apr. 23, 2010.
Supplemental European Search Report issued for EP 07795522.7 dated Feb. 25, 2010.
Supplemental European Search Report issued for EP 07775978.5 dated Jul. 6, 2009.
Bitzan et al., "Safety and pharmacokinetics of chimeric anti-shiga toxin-1 and anti-shiga toxin 2 monoclonal antibodies in healthy volunteers," *Antimicrob. Agents Chemother.* 53: 3081-3087 (2009).
Melton-Celsa et al., "Protective efficacy, toxicity and pharmacokinetic evaluation in mice of human/mouse chimeric antibosies to Stx1 and Stx2," *Abstr. Gen. Meet. Am. Soc. Microbiol.* 102: 12, May 19-23, 2002.
Sauter et al., "Mouse model of hemolytic-uremic syndrome caused by endotoxin-free shiga toxin 2 (Stx2) and protection from lethal outcome by anti-stx2 antibody," *Infect. Immun.* 76: 4469-4478 (2008).
Smith et al., "Monoclonal antibody 11E10, which neutralizes shiga toxin type 2 (Stx2), recognizes three regions on the Stx2 a subunit, blocks the enzymatic action of the toxin in vitro, and alters the overall cellular distribution of the toxin," *Infect. Immun.* 77: 2730-2740 (2009).
Co et al., "Humanized Antibodies for Therapy," *Nature* 351:501-502 (1991).
Harari et al., "Carboxy-terminal Peptides from the B Subunit of Shiga Toxin Induce a Local and Parenteral Protective Effect," *Molecular Immunology* 27:613-621 (1990).
Strockbine et al., "Two Toxin-Converting Phages from *Escherichia coli* O157:H7 Strain 933 Encode Antigenically Distinct Toxins with Similar Biologic Activities," *Infect. Immun.* 53:135-140 (1986).
Notice of Reasons of Rejection for Japanese Application No. 2000-525563, dated Nov. 11, 2008 (English Translation).
Summons to attend oral proceedings pursuant to Rule 115(1) EPC for European Application No. 07795522.7, dated Dec. 22, 2011.
Extended European Search Report for European Application No. 07775978.5, dated Jul. 23, 2009.
Extended European Search Report for European Application No. 11179552.2, dated Jan. 20, 2012.
International Preliminary Report on Patentability and Written Opinion of the International Searching Authority for International Application No. PCT/US2007/012797, dated Dec. 3, 2008.
International Search Report for International Application No. PCT/US2007/012797, dated Jan. 10, 2008.
International Preliminary Report on Patentability and Written Opinion of the International Searching Authority for International Application No. PCT/US2010/021610, dated Jul. 26, 2011.
GenBank Accession No. AB083044.1, "*Escherichia coli* O157:H7 Stx1 Genes for Shiga Toxin 1 Variant A Subunit, Shiga Toxin 1 Variant B Subunit, Complete Cds, Strain:AI2001/52," 2003.
López et al., "Shigatec Trial: A Phase II Study Assessing Monoclonal Antibodies Against Shiga Toxin 1 and 2 in Shiga Toxin-producing *E. coil*-infected Children," Poster Presentation at the 49$^{th}$ IDSA Annual Meeting, Boston, USA, Oct. 20-23, 2011.
Ofek et al., "Elicitation of Structure-Specific Antibodies by Epitope Scaffolds," *Proc. Natl. Acad. Sci. U.S.A.* 107: 17880-17887, 2010.
EPO Communication for European Application No. 07 775 978, dated Jan. 10, 2012.
Examiner's Report for Australian Application No. 2007240614, dated Dec. 15, 2011.

* cited by examiner

Stx2

Stx

Figure 3.

Stx1 operon DNA sequence (from StxA1 start codon to StxB1 stop codon) (SEQ ID NO: 5):

```
1  ATGAAAATAA TTATTTTTAG AGTGCTAACT TTTTTCTTTG TTATCTTTTC AGTTAATGTG
61  GTGGCGAAGG AATTTACCTT AGACTTCTCG ACTGCAAAGA CGTATGTAGA TTCGCTGAAT
121  GTCATTCGCT CTGCAATAGG TACTCCATTA CAGACTATTT CATCAGGAGG TACGTCTTTA
181  CTGATGATTG ATAGTGGCTC AGGGGATAAT TTGTTTGCAG TTGATGTCAG AGGGATAGAT
241  CCAGAGGAAG GGCGGTTTAA TAATCTACGG CTTATTGTTG AACGAAATAA TTTATATGTG
301  ACAGGATTTG TTAACAGGAC AAATAATGTT TTTTATCGCT TTGCTGATTT TTCACATGTT
361  ACCTTTCCAG GTACAACAGC GGTTACATTG TCTGGTGACA GTAGCTATAC CACGTTACAG
421  CGTGTTGCAG GGATCAGTCG TACGGGGATG CAGATAAATC GCCATTCGTT GACTACTTCT
481  TATCTGGATT TAATGTCGCA TAGTGGAACC TCACTGACGC AGTCTGTGGC AAGAGCGATG
541  TTACGGTTTG TTACTGTGAC AGCTGAAGCT TTACGTTTTC GGCAAATACA GAGGGGATTT
601  CGTACAACAC TGGATGATCT CAGTGGGCGT TCTTATGTAA TGACTGCTGA AGATGTTGAT
661  CTTACATTGA ACTGGGGAAG GTTGAGTAGC GTCCTGCCTG ACTATCATGG ACAAGACTCT
721  GTTCGTGTAG GAAGAATTTC TTTTGGAAGC ATTAATGCAA TTCTGGGAAG CGTGGCATTA
781  ATACTGAATT GTCATCATCA TGCATCGCGA GTTGCCAGAA TGGCATCTGA TGAGTTTCCT
841  TCTATGTGTC CGGCAGATGG AAGAGTCCGT GGGATTACGC ACAATAAAAT ATTGTGGGAT
901  TCATCCACTC TGGGGGCAAT TCTGATGCGC AGAACTATTA GCAGTTGAGG GGGTAAAATG
961  AAAAAAACAT TATTAATAGC TGCATCGCTT TCATTTTTTT CAGCAAGTGC GCTGGCGACG
1021  CCTGATTGTG TAACTGGAAA GGTGGAGTAT ACAAAATATA ATGATGACGA TACCTTTACA
1081  GTTAAAGTGG GTGATAAAGA ATTATTTACC AACAGATGGA ATCTTCAGTC TCTTCTTCTC
1141  AGTGCGCAAA TTACGGGGAT GACTGTAACC ATTAAAACTA ATGCCTGTCA TAATGGAGGG
1201  GGATTCAGCG AAGTTATTTT TCGTTGA
```

stxA1 DNA Sequence (from StxA1 start codon to StxA1 stop codon) (SEQ ID NO:6):

```
  1  ATGAAAATAA TTATTTTTAG AGTGCTAACT TTTTTCTTTG TTATCTTTTC AGTTAATGTG
 61  GTGGCGAAGG AATTTACCTT AGACTTCTCG ACTGCAAAGA CGTATGTAGA TTCGCTGAAT
121  GTCATTCGCT CTGCAATAGG TACTCCATTA CAGACTATTT CATCAGGAGG TACGTCTTTA
181  CTGATGATTG ATAGTGGCTC AGGGGATAAT TTGTTTGCAG TTGATGTCAG AGGGATAGAT
241  CCAGAGGAAG GGCGGTTTAA TAATCTACGG CTTATTGTTG AACGAAATAA TTTATATGTG
301  ACAGGATTTG TTAACAGGAC AAATAATGTT TTTTATCGCT TTGCTGATTT TTCACATGTT
361  ACCTTTCCAG GTACAACAGC GGTTACATTG TCTGGTGACA GTAGCTATAC CACGTTACAG
421  CGTGTTGCAG GGATCAGTCG TACGGGGATG CAGATAAATC GCCATTCGTT GACTACTTCT
481  TATCTGGATT TAATGTCGCA TAGTGGAACC TCACTGACGC AGTCTGTGGC AAGAGCGATG
541  TTACGGTTTG TTACTGTGAC AGCTGAAGCT TTACGTTTTC GGCAAATACA GAGGGGATTT
601  CGTACAACAC TGGATGATCT CAGTGGGCGT TCTTATGTAA TGACTGCTGA AGATGTTGAT
661  CTTACATTGA ACTGGGGAAG GTTGAGTAGC GTCCTGCCTG ACTATCATGG ACAAGACTCT
721  GTTCGTGTAG GAAGAATTTC TTTTGGAAGC ATTAATGCAA TTCTGGGAAG CGTGGCATTA
781  ATACTGAATT GTCATCATCA TGCATCGCGA GTTGCCAGAA TGGCATCTGA TGAGTTTCCT
841  TCTATGTGTC CGGCAGATGG AAGAGTCCGT GGGATTACGC ACAATAAAAT ATTGTGGGAT
901  TCATCCACTC TGGGGGCAAT TCTGATGCGC AGAACTATTA GCAGTTGA
```

Figure 3 cont.

stxB1 DNA Sequence (from StxB1 start codon to StxB1 stop codon) (SEQ ID NO: 7):

```
  1  ATGAAAAAAA CATTATTAAT AGCTGCATCG CTTTCATTTT TTTCAGCAAG TGCGCTGGCG
 61  ACGCCTGATT GTGTAACTGG AAAGGTGGAG TATACAAAAT ATAATGATGA CGATACCTTT
121  ACAGTTAAAG TGGGTGATAA AGAATTATTT ACCAACAGAT GGAATCTTCA GTCTCTTCTT
181  CTCAGTGCGC AAATTACGGG GATGACTGTA ACCATTAAAA CTAATGCCTG TCATAATGGA
241  GGGGGATTCA GCGAAGTTAT TTTTCGTTGA
```

StxA1 protein sequence (processed leader sequence is underlined) (SEQ ID NO: 8):

```
  1  MKIIIFRVLT FFFVIFSVNV VAKEFTLDFS TAKTYVDSLN VIRSAIGTPL QTISSGGTSL
 61  LMIDSGSGDN LFAVDVRGID PEEGRFNNLR LIVERNNLYV TGFVNRTNNV FYRFADFSHV
121  TFPGTTAVTL SGDSSYTTLQ RVAGISRTGM QINRHSLTTS YLDLMSHSGT SLTQSVARAM
181  LRFVTVTAEA LRFRQIQRGF RTTLDDLSGR SYVMTAEDVD LTLNWGRLSS VLPDYHGQDS
241  VRVGRISFGS INAILGSVAL ILNCHHHASR VARMASDEFP SMCPADGRVR GITHNKILWD
301  SSTLGAILMR RTISS
```

StxB1 protein sequence (processed leader sequence is underlined) (SEQ ID NO: 9):

```
  1  MKKTLLIAAS LSFFSASALA TPDCVTGKVE YTKYNDDDTF TVKVGDKELF TNRWNLQSLL
 61  LSAQITGMTV TIKTNACHNG GGFSEVIFR
```

stx2 operon DNA sequence (from StxA2 start codon to StxB2 stop codon) (SEQ ID NO: 10):

```
   1  ATGAAGTGTA TATTATTTAA ATGGGTACTG TGCCTGTTAC TGGGTTTTTC TTCGGTATCC
  61  TATTCCCGGG AGTTTACGAT AGACTTTTCG ACCCAACAAA GTTATGTCTC TTCGTTAAAT
 121  AGTATACGGA CAGAGATATC GACCCCTCTT GAACATATAT CTCAGGGGAC CACATCGGTG
 181  TCTGTTATTA ACCACACCCC ACCGGGCAGT TATTTTGCTG TGGATATACG AGGGCTTGAT
 241  GTCTATCAGG CGCGTTTTGA CCATCTTCGT CTGATTATTG AGCAAAATAA TTTATATGTG
 301  GCCGGGTTCG TTAATACGGC AACAAATACT TTCTACCGTT TTTCAGATTT TACACATATA
 361  TCAGTGCCCG GTGTGACAAC GGTTTCCATG ACAACGGACA GCAGTTATAC CACTCTGCAA
 421  CGTGTCGCAG CGCTGGAACG TTCCGGAATG CAAATCAGTC GTCACTCACT GGTTTCATCA
 481  TATCTGGCGT TAATGGAGTT CAGTGGTAAT ACAATGACCA GAGATGCATC CAGAGCAGTT
 541  CTGCGTTTTG TCACTGTCAC AGCAGAAGCC TTACGCTTCA GGCAGATACA GAGAGAATTT
 601  CGTCAGGCAC TGTCTGAAAC TGCTCCTGTG TATACGATGA CGCCGGGAGA CGTGGACCTC
 661  ACTCTGAACT GGGGGCGAAT CAGCAATGTG CTTCCGGAGT ATCGGGGAGA GGATGGTGTC
 721  AGAGTGGGGA GAATATCCTT TAATAATATA TCAGCGATAC TGGGGACTGT GGCCGTTATA
 781  CTGAATTGCC ATCATCAGGG GGCGCGTTCT GTTCGCGCCG TGAATGAAGA GAGTCAACCA
 841  GAATGTCAGA TAACTGGCGA CAGGCCTGTT ATAAAAATAA ACAATACATT ATGGGAAAGT
 901  AATACAGCTG CAGCGTTTCT GAACAGAAAG TCACAGTTTT TATATACAAC GGGTAAATAA
 961  AGGAGTTAAG CATGAAGAAG ATGTTTATGG CGGTTTTATT TGCATTAGCT TCTGTTAATG
1021  CAATGGCGGC GGATTGTGCT AAAGGTAAAA TTGAGTTTTC CAAGTATAAT GAGGATGACA
1081  CATTTACAGT GAAGGTTGAC GGGAAAGAAT ACTGGACCAG TCGCTGGAAT CTGCAACCGT
1141  TACTGCAAAG TGCTCAGTTG ACAGGAATGA CTGTCACAAT CAAATCCAGT ACCTGTGAAT
1201  CAGGCTCCGG ATTTGCTGAA GTGCAGTTTA ATAATGACTG A
```

Figure 3 cont.

stx$A_2$ DNA Sequence (from StxA2 start codon to StxA2 stop codon) (SEQ ID NO: 11):

```
  1 ATGAAGTGTA TATTATTTAA ATGGGTACTG TGCCTGTTAC TGGGTTTTTC TTCGGTATCC
 61 TATTCCCGGG AGTTTACGAT AGACTTTTCG ACCCAACAAA GTTATGTCTC TTCGTTAAAT
121 AGTATACGGA CAGAGATATC GACCCCTCTT GAACATATAT CTCAGGGGAC CACATCGGTG
181 TCTGTTATTA ACCACACCCC ACCGGGCAGT TATTTTGCTG TGGATATACG AGGGCTTGAT
241 GTCTATCAGG CGCGTTTTGA CCATCTTCGT CTGATTATTG AGCAAAATAA TTTATATGTG
301 GCCGGGTTCG TTAATACGGC AACAAATACT TTCTACCGTT TTTCAGATTT TACACATATA
361 TCAGTGCCCG GTGTGACAAC GGTTTCCATG ACAACGGACA GCAGTTATAC CACTCTGCAA
421 CGTGTCGCAG CGCTGGAACG TTCCGGAATG CAAATCAGTC GTCACTCACT GGTTTCATCA
481 TATCTGGCGT TAATGGAGTT CAGTGGTAAT ACAATGACCA GAGATGCATC CAGAGCAGTT
541 CTGCGTTTTG TCACTGTCAC AGCAGAAGCC TTACGCTTCA GGCAGATACA GAGAGAATTT
601 CGTCAGGCAC TGTCTGAAAC TGCTCCTGTG TATACGATGA CGCCGGGAGA CGTGGACCTC
661 ACTCTGAACT GGGGGCGAAT CAGCAATGTG CTTCCGGAGT ATCGGGGAGA GGATGGTGTC
721 AGAGTGGGGA GAATATCCTT TAATAATATA TCAGCGATAC TGGGGACTGT GGCCGTTATA
781 CTGAATTGCC ATCATCAGGG GGCGCGTTCT GTTCGCGCCG TGAATGAAGA GAGTCAACCA
841 GAATGTCAGA TAACTGGCGA CAGGCCTGTT ATAAAAATAA ACAATACATT ATGGGAAAGT
901 AATACAGCTG CAGCGTTTCT GAACAGAAAG TCACAGTTTT TATATACAAC GGGTAAATAA
```

StxB2 DNA Sequence (from StxB2 start codon to StxB2 stop codon) (SEQ ID NO: 12):

```
  1 ATGAAGAAGA TGTTTATGGC GGTTTTATTT GCATTAGCTT CTGTTAATGC AATGGCGGCG
 61 GATTGTGCTA AAGGTAAAAT TGAGTTTTCC AAGTATAATG AGGATGACAC ATTTACAGTG
121 AAGGTTGACG GGAAAGAATA CTGGACCAGT CGCTGGAATC TGCAACCGTT ACTGCAAAGT
181 GCTCAGTTGA CAGGAATGAC TGTCACAATC AAATCCAGTA CCTGTGAATC AGGCTCCGGA
241 TTTGCTGAAG TGCAGTTTAA TAATGACTGA
```

StxA2 protein sequence (processed leader sequence is underlined) (SEQ ID NO: 13):

1 <u>MKCILFKWVL CLLLGFSSVS Y</u>SREFTIDFS TQQSYVSSLN SIRTEISTPL EHISQGTTSV
 61 SVINHTPPGS YFAVDIRGLD VYQARFDHLR LIIEQNNLYV AGFVNTATNT FYRFSDFTHI
121 SVPGVTTVSM TTDSSYTTLQ RVAALERSGM QISRHSLVSS YLALMEFSGN TMTRDASRAV
181 LRFVTVTAEA LRFRQIQREF RQALSETAPV YTMTPGDVDL TLNWGRISNV LPEYRGEDGV
241 RVGRISFNNI SAILGTVAVI LNCHHQGARS VRAVNEESQP ECQITGDRPV IKINNTLWES
301 NTAAAFLNRK SQFLYTTGK

StxB2 protein sequence(processed leader sequence is underlined) (SEQ ID NO: 14):

1 <u>MKKMFMAVLF ALASVNAMAA</u> DCAKGKIEFS KYNEDDTFTV KVDGKEYWTS RWNLQPLLQS
61 AQLTGMTVTI KSSTCESGSG FAEVQFNND

A

```
                 10        20        30        40        50
                  *         *         *         *         *
StxB2  -ADCAKGKIEFSKYNEDDTFTVKVDGKEYWTSRWNLQPLLQSAQLTGMTVT
StxB1  TP..VT..V.YT...D........GD..LF.N.....S..L...I......
        1                        2

             60        70
              *         *
StxB2  IKSSTCESGSGFAEVQFNND
StxB1  ..TNA.HN.G..S..I.R-
           3
```

Figure 8

```
                  10        20        30        40        50
                   *         *         *         *         *
Stx1     MKKTLLIAASLSFFSASALATPDCVTGKVEYTKYNDDDTFTVKVGDKELF
Stx1c    ...I.............V..A.............................
Stx1d    ...V....V....L...V..A.......................A.....

                  60        70        80
                   *         *         *
Stx1     TNRWNLQSLLLSAQITGMTVTIKTNACHNGGGFSEVIFR
Stx1c    .......................................
Stx1d    ........................T..............
```

METHODS AND COMPOSITIONS BASED ON SHIGA TOXIN TYPE 1 PROTEIN

CROSS-REFERENCE TO RELATED APPLICATION

This application claims benefit of U.S. Provisional Application No. 60/793,918, filed Apr. 20, 2006, which is hereby incorporated by reference.

STATEMENT AS TO FEDERALLY SPONSORED RESEARCH

The present research was supported by grants from the NIH (No. AI20148) and Department of Defense (No. R073KD). The U.S. government therefore may have certain rights to this invention.

BACKGROUND OF THE INVENTION

In general, this invention relates to the field of treating and preventing Shiga toxin associated diseases.

In the United States, Shiga toxin (Stx)-producing *Escherichia coli* (STEC) account for about 110,000 infections per year. Enterohemorrhagic *E. coli* (EHEC), most notably the serotype O157:H7, is a subset of STEC that is noted for producing Stx mediated disease. A possible complication from an infection with a Stx-producing organism is the hemolytic uremic syndrome (HUS), which is characterized by hemolytic anemia, thrombic thrombocytopenia, and renal failure. There is approximately a 5-10% fatality rate for those with HUS and survivors may have lasting kidney damage. Currently there are no FDA approved therapies or vaccines to combat or prevent illness from a Stx-mediated disease, but several promising options for the future include: a humanized monoclonal antibody that binds to and neutralizes Stx2 and a chimeric StxA2/StxB1 toxoid that elicits a neutralizing response and provides protection against a lethal challenge of Stx1 or Stx2 or Stx1 and Stx2.

There are essentially two main types of Stxs: Stx/Stx1 and Stx2. Stx is produced from *Shigella dysenteriae* type 1, while Stx1 and Stx2 are produced from *Escherichia coli*. Stx and Stx1 are virtually identical, with only one amino acid difference in the A subunit. The mature A and B subunits of Stx1 and Stx2 have 68 and 73% similarity, respectively. Despite the amino acid sequence differences, the crystal structures of Stx and Stx2 are remarkably similar (FIG. 1). These toxins can be differentiated by polyclonal antisera: polyclonal antisera raised against Stx1 does not neutralize Stx2 and vice-versa. Variants of Stx1 and Stx2 exist and include Stx1c, Stx1 d, Stx2c, Stx2d, Stx2d-activatable (Stx2-act.), Stx2e, and Stx2f.

Shiga toxins are complex holotoxins with an $AB_5$ structure. The active domain (A), contains an N-glycosidase that depurinates the 28S rRNA of the 60S ribosomal subunit, which stops proteins synthesis and eventually leads to cell death. The A subunit is ~32 kDa and is proteolytically cleaved by trypsin or furin into a ~28 kDa $A_1$ subunit and a ~5 kDa $A_2$ peptide which are connected through a single disulphide bond. The $A_1$ subunit contains the active domain, and the $A_2$ peptide non-covalently tethers the active domain to the binding domain. The binding domain (B) consists of five identical ~7.7 kDa monomers that form a pentamer through which the C-terminus of the $A_2$ peptide traverses. Each of the B subunit monomers has two cysteine residues that form a disulphide bond within each monomer (FIG. 2). The B pentamer binds the eukaryotic receptor globotriaosyl ceramide ($Gb_3$) (or $Gb_4$ as is the case for Stx2e).

Despite this knowledge about the results of exposure to these toxins, currently there is no known cure or vaccine for HUS. The use of antibiotics may exacerbate the situation by increasing toxin release from bacteria. Thus, there is a need for a compound to prevent or to treat the complications of EHEC produced by Shiga toxin. Such a compound could be used to treat infected subjects and decrease the systemic effects of toxin on the CNS, blood, and kidneys. In addition, if the toxin could be neutralized, antibiotics could be safely given to kill the bacteria in the GI tract. Such a compound could also be used to prevent infectious complications, by treating exposed or high risk individuals before they acquire EHEC infection. Such individuals would include children in day care or the elderly in nursing homes, where a case of EHEC diarrhea has been identified. These individuals are at increased risk to develop EHEC, often with severe complications, and spread of EHEC in these environments is not unusual.

SUMMARY OF THE INVENTION

Monoclonal antibody (MAb) 13C4 recognizes the B subunit of Stx1 and neutralizes its cytotoxicity. Despite the 73% amino acid (aa) sequence similarity between StxB1 and StxB2, the 13C4 MAb does not bind to StxB2. We have discovered that the 13C4 epitope encompasses regions of dissimilarity between StxB1 and StxB2. The 13C4 MAb recognizes a discontinuous or conformational epitope that spans three regions on the StxB1 monomer and requires residue 55. The three regions of dissimilarity, (aa 1-6 (SEQ ID No: 1), 25-32 (SEQ ID NO:2) and 54-61 (SEQ ID NO: 3)), are found to be located near each other on the crystal structure of StxB (StxB is identical to StxB1). Each of the two flanking regions (1-6, 54-61) contains a cysteine residue. The 13C4 epitope therefore includes at least one, two, or all three of the sequences set forth in SEQ ID NOs: 1, 2, and 3.

Accordingly, the invention features a method of producing anti-Stx1 antibodies (e.g., monoclonal and polyclonal antibodies) and antibody fragments which specifically bind to the 13C4 epitope of Stx1. Such antibodies or antibody fragments specifically bind to Stx1 and not Stx2. This method includes the immunization of a mammal with a polypeptide that includes a fragment of Stx1 (i.e., not full length Stx1) that includes at least one, two, or three of the three sequences set forth in SEQ ID NOs: 1, 2, and 3, where this polypeptide does not include full length Stx1. Preferably the method includes the use of Stx1 that includes SEQ ID NOs: 1 and 3. In one embodiment, the method includes immunization of the mammal with a polypeptide substantially identical to the amino acid sequence set forth in SEQ ID NO: 4, which includes SEQ ID NOs: 1, 2, and 3.

The anti-Stx1 antibodies can be screened using standard methods known in the art or described herein including, for example, the in vitro neutralization assay described herein, to identify antibodies that specifically bind to Stx1 and not Stx2. The immunogenic polypeptide, and methods of preparing this polypeptide, along with the nucleic acid molecule that encodes this polypeptide (including where this nucleic acid is linked to an expression construct in a vector, and where this vector is inserted into a host cell), are also included as related aspects of the invention.

This invention also features anti-Stx1 antibodies that specifically bind to the 13C4 epitope of Stx1, where the antibodies specifically bind to Stx1 and not Stx2. Preferred antibodies of the invention bind to an epitope that includes at least one, two, or all three of the sequences set forth in SEQ ID NOs: 1, 2, and 3, preferably to a binding site formed by SEQ ID NOs: 1 and 3, and most preferably containing all three. The epitope can be a conformational epitope where the amino acid sequences are in proximity based on the conformation of the Stx1 polypeptide that includes the epitope or a Stx 2 chimeric protein containing the 3 epitope regions (SEQ ID NOs: 1, 2, and 3) present in the Stx1 protein. The antibodies can be IgG, IgM, IgE, IgD, IgA, Fab, Fv, monoclonal and polyclonal antibodies, or antibody fragments and can be developed by the methods described herein. The antibodies preferably bind Stx1 with a $K_d$ of less than 100 nM, 50 nM, 10 nM, 1 nM, 100 pM, 10 pM, or 1 pM or less. In one example, the antibody of the invention inhibits binding of the 13C4 antibody to Stx1 or a chimeric protein containing the 13C4 epitope, including an inhibition with a $K_d$ value of between 100 nM-1 pM. Also, desirably, the antibodies inhibit Stx1 binding to the eukaryotic receptor globotriaosyl ceramide (Gb3). The anti-Stx1 antibodies of the invention are not meant to include the mouse, humanized, or chimeric forms of the 13C4, monoclonal 5-5B, or 2H3 antibodies. The invention further includes a hybridoma cell line that produces any of the antibodies of the invention.

Another aspect of the invention is a composition for stimulating an immune response against Stx1 using at least one peptide, where the peptide includes, at least one, two, or three of the sequences set forth in SEQ ID NOs: 1, 2, and 3 and where the peptide is not full length Stx1. The composition can further include an adjuvant. Desirably, the peptide includes an amino acid sequence substantially identical to the amino acid sequence set forth in SEQ ID NO: 4, or a fragment thereof. The invention also features the use of a chimeric peptide including a 13C4 epitope (e.g., a chimeric peptide containing at least one, two, or all three of SEQ ID NOs: 1, 2, or 3 inserted into a scaffold protein such as StxB2). This peptide can be used to immunize against or treat, any Shiga toxin associated disease including hemolytic uremia syndrome and diseases associated with *E. coli* and *S. dysenteriae* infection.

Yet another aspect of the invention features a method of detecting Stx1 in a biological sample (e.g., tissue, cell, cell extract, bodily fluid, and biopsy) using any of the antibodies of the invention. Detection methods of the invention include ELISA, RIA, western blotting, immunoprecipitation, and flow cytometry. The invention includes the diagnosis of a Shiga toxin associated disease based on the identification of Stx1 in a sample. The invention also features an immunological test kit for detecting a Shiga toxin associated disease, the kit including an antibody of the invention and a means for detecting the antibody.

Yet another aspect of the invention features a method of treating a Shiga toxin associated disease using an antibody produced by any of the forgoing methods. Examples of Shiga toxin associated diseases include hemolytic uremia syndrome (HUS) and diseases associated with *E. coli* and *S. dysenteriae* infection. These antibodies can be administered in combination with other therapies, including, but not limited to, antibodies that specifically bind other Shiga toxin associated proteins (e.g., Stx2).

By "13C4 epitope" is meant a sequence of amino acids which, either as a result of linear structure or three dimensional conformation, forms the binding site for the 13C4 antibody. This term is meant to include any non-full length Stx1 protein that includes sequences substantially identical to one, two, or three of the sequences set forth in SEQ ID NOs: 1, 2, and 3 (e.g., SEQ ID NOs: 1 and 2, SEQ ID NOs: 2 and 3, SEQ ID NOs: 1 and 3, and SEQ ID NOs: 1, 2, and 3). One example of a protein that includes a 13C4 epitope is a protein that includes an amino acid sequence substantially identical to the amino acid sequence set forth in SEQ ID NO: 4.

By the terms "antibody that specifically binds to the 13C4 epitope of Stx1" or "13C4 epitope-specific antibody" is meant an antibody that binds to an Stx1 protein that includes the 13C4 epitope with a $K_d$ value of between 100 nM-1 pM. Such antibodies are also characterized by little or no detectable binding to the to the Stx2 protein (e.g., having a $K_d$ value of greater than 100 nM, 200 nM, 500 nM, 1 μM, 10 μM, 100 μM, 1 mM or greater for Stx2). Antibody affinities may be determined using any of the assays known in the art including, but not limited to, surface plasmon resonance based assay, enzyme-linked immunoabsorbent assay (ELISA), and competition assays (e.g. RIA's). Also, the antibody may be subjected to an in vitro neutralization assay as described herein. An antibody that binds specifically to the 13C4 epitope will neutralize the cytotoxic effect of Stx1 by at least 10%, 20%, 30%, 40%, 50%, 75%, or greater, using the assays described herein or known in the art.

By "inhibit binding" is meant a to cause a decrease a protein binding to another protein by at least 50%, preferably 60%, 70%, 80%, 90%, or more, as measured, for example, by ELISA or the $Gb_3$ receptor binding assay described herein.

The term "antibody" is used in the broadest sense and includes monoclonal antibodies (including full length monoclonal antibodies), polyclonal antibodies, multispecific antibodies (e.g., bispecific antibodies), or antibody fragments, provided such molecules possess a desired biological activity (e.g., neutralization of the Stx1 toxin as described herein).

By "isolated" is meant a protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes.

By "non-full length Stx1" is meant a protein that contains fewer than 90%, 80%, 70%, 60%, or fewer amino acids of the full length Stx1 polypeptide.

By "substantially identical" is meant a nucleic acid or amino acid sequence that, when optimally aligned, for example using the methods described below, share at least 75%, 80%, 85%, 90%, 95%, 96%, 97%, 98%, 99%, or 100% sequence identity with a second nucleic acid or amino acid sequence, e.g., a Stx1, Stx2, or chimera protein such as the one set forth in SEQ ID NO: 4. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) *J. Mol. Biol.* 147:195-7); "Best Fit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) *J. Mol. Biol.* 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences can be at least 6 amino acids, preferably 10, 20, 30, 40, 50, 60, or 70 amino acids or more up to the entire length of the protein. For nucleic acids, the length of comparison sequences can generally be at least 18, 25, 50, 100, 150, or 200 nucleotides or more up to the entire length of the nucleic acid molecule. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, 100, 200, or more nucleotides or 10, 20, 30, 40, 50, 60, or 70 amino acids or more. Fragments of Shiga toxin type 1 or Shiga toxin type 2 protein can include any portion that is less than the full-length protein (put in the full length size as a reference point and then specify exemplary lengths). Fragments can also include Stx1 or 2 subunits such as Stx B1 and B2.

By "Shiga toxin associated disease" is meant any disease resulting from a pathogen expressing a Shiga toxin. The term "Shiga toxin associated disease" is meant to include hemolytic uremia syndrome, shigellosis, and diseases resulting from Shiga toxin-producing *Escherichia coli* and *S. dysenteriae* infection.

BRIEF DESCRIPTION OF THE FIGURES

FIG. 3 shows the nucleic acid and amino acid sequences of the indicated Stx proteins.

FIG. 8 shows an amino acid alignment of the B subunits from Stx1, Stx1c and Stx1d (SEQ ID NO: 9). The 20 amino acid leader sequence that is removed to generate the mature protein is underlined in Stx1. The three amino acid differences between StxB1 and StxBd1 are boxed. The arrow indicates a conserved amino acid residue and the remaining indicated Stx1c and Stx1d amino acid residues are non-conserved amino acids. The dots indicate identical amino acids.

DETAILED DESCRIPTION OF THE INVENTION

Figure 1:
FIG. 1 shows the crystal Structure of Stx and Stx2.
Figure 2:
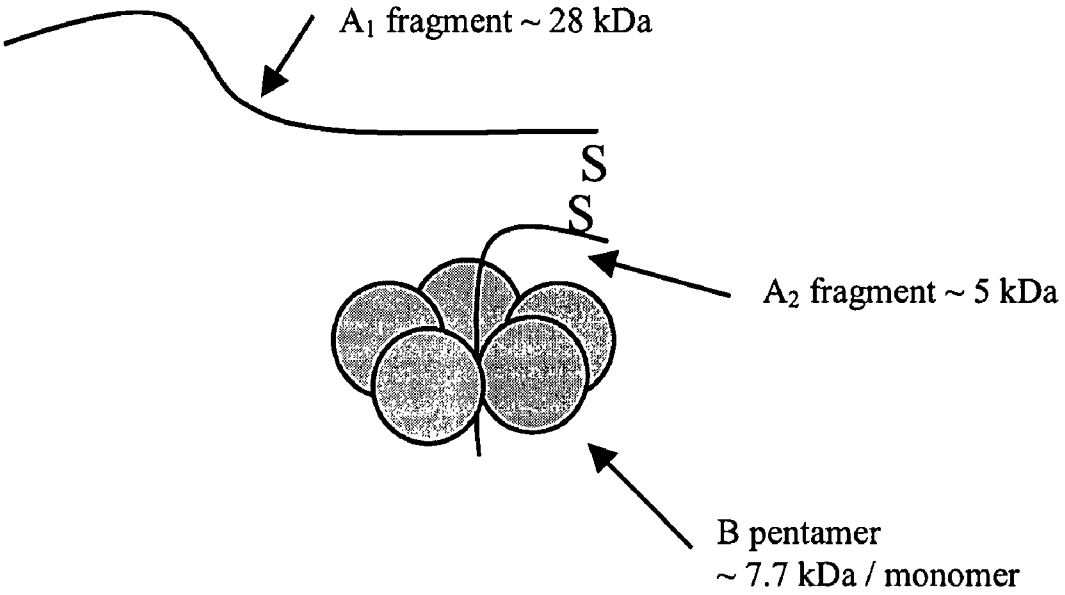
FIG. 2 shows the general Shiga toxin structure.

In general, the invention features the production of antibodies that specifically bind to the 13C4 epitope of the Stx1 protein. We have discovered the 13C4 epitope and have found that this epitope includes at least one, two, or three of the sequences set forth in SEQ ID NOs: 1, 2, and 3. We have also discovered that a subject having, or at risk of developing, a Shiga toxin associated disease (e.g., hemolytic uremia syndrome and diseases associated with *E. coli* and *S. dysenteriae* infection) can be treated with a peptide containing the 13C4 epitope or with antibodies that specifically bind to the 13C4 epitope of the Stx1 protein.

I. Indications

The compounds and methods of the invention are useful for treating subjects having, or at risk of developing a Shiga toxin associated disease. Such subjects would include children in day care or the elderly in nursing homes. In one example, the subject is in a day care or in a nursing home where a case of EHEC diarrhea has been detected. In this example, the subject may or may not have developed the disease. Shiga toxin associated diseases include those resulting from infection with Shiga toxin producing *S. dysenteriae* or Enterohemorrhagic *E. coli* (EHEC), most notably the serotype O157:H7. These infections often result in hemolytic uremic syndrome (HUS), which is characterized by hemolytic anemia, thrombotic thrombocytopenia, and renal failure.

II. Antibodies

The invention includes the production of antibodies which specifically bind to the 13C4 epitope of the Shiga toxin type I (Stx1) protein. Desirably, such an antibody-does not detectably bind to Stx2. The unique ability of antibodies to recognize and specifically bind to target proteins provides approaches for both diagnosing and treating diseases related to Shiga toxin-producing *Escherichia coli* (STEC). The invention provides for the production of antibodies, including, but not limited to, polyclonal and monoclonal antibodies, anti-idiotypic antibodies, murine and other mammalian antibodies, antibody fragments, bispecific antibodies, antibody dimers or tetramers, single chain antibodies (e.g., scFv's and antigen-binding antibody fragments such as Fabs, diabodies, and Fab' fragments), recombinant binding regions based on antibody binding regions, chimeric antibodies, primatized antibodies, humanized and fully human antibodies, domain deleted antibodies, and antibodies labeled with a detectable marker, or coupled with a toxin or radionucleide. Such antibodies are produced by conventional methods known in the art. In one aspect, the invention includes the preparation of monoclonal antibodies or antibody fragments that specifically bind to the 13C4 epitope of Stx1 where the preparation includes the use of a non-full length fragment of Stx1 which contains at least one, two, or three sequences selected from the sequences set forth in SEQ ID NOs: 1, 2, or 3. One example of such a fragment is the protein of SEQ ID NO: 4.

Polyclonal Antibodies

Polyclonal antibodies can be prepared by immunizing rabbits or other animals by injecting antigen followed by subsequent boosts at appropriate intervals. The animals are bled and the sera is assayed against purified protein usually by ELISA.

Polyclonal antibodies that specifically bind to the 13C4 epitope can be raised in animals by multiple subcutaneous (sc) or intraperitoneal (ip) injections of the antigen and an adjuvant. It may be useful to conjugate the antigen or a fragment containing the target amino acid sequence to a protein that is immunogenic in the species to be immunized (e.g., keyhole limpet hemocyanin, serum albumin, bovine thyroglobulin, or soybean trypsin inhibitor) using a bifunctional or derivatizing agent (e.g., maleimidobenzoyl sulfosuccinimide ester (conjugation through cysteine residues), N-hydroxysuccinimide (through lysine residues), glutaraldehyde, or succinic anhydride).

For example, animals can be immunized against the 13C4 epitope, immunogenic conjugates, or derivatives by combining 1 μg to 1 mg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer to the antigen or a fragment thereof. Animals are boosted until the titer plateaus. Preferably, the animal is boosted with the conjugate of the same polypeptide, but conjugated to a different protein and/or through a different cross-linking reagent. Conjugates also can be made in recombinant cell culture as protein fusions. Also, aggregating agents such as alum are suitably used to enhance the immune response.

Chimeric, humanized, or fully human polyclonals may be produced in animals transgenic for human immunoglobulin genes, or by isolating two or more Stx1 reactive B-lymphocytes from a subject for starting material.

Polyclonals may also be purified and selected for (such as through affinity for a conformationally constrained antigen peptide), iteratively if necessary, to provide a monoclonal antibody. Alternatively or additionally, cloning out the nucleic acid encoding a single antibody from a lymphocyte may be employed.

Monoclonal Antibodies

In another embodiment of the invention, monoclonal antibodies are obtained from a population of substantially homogeneous antibodies (i.e., the individual antibodies including the population are identical except for possible naturally occurring mutations that may be present in minor amounts). Thus, the term monoclonal indicates the character of the antibody as not being a mixture of discrete antibodies.

Monoclonal antibodies can be prepared by methods known in the art, such as the hybridoma method of Kohler and Milstein by fusing splenocytes from immunized mice with continuously replicating tumor cells such as myeloma or lymphoma cells. (Kohler and Milstein (1975) Nature 256: 495-497; Gulfre and Milstein (1981) Methods in Enzymology: Immunochemical Techniques 73: 1-46, Langone and Banatis eds., Academic Press). The hybridoma cells are then cloned by limiting dilution methods and supernates assayed for antibody production by ELISA, RIA, or bioassay. In another embodiment, monoclonals may be made by recombinant DNA methods.

For preparation of monoclonal antibodies (Mabs) that specifically bind the 13C4 epitope, any technique that provides for the production of antibody molecules by continuous cell lines in culture may be used. For example, the hybridoma technique originally developed by Kohler and Milstein ((1975) supra, as well as in Kohler and Milstein (1976) Eur J Immunol. 6: 511-519; Kohler et al. (1976) Eur J Immunol. 6: 292-295; Hammerling et al. (1981) in: Monoclonal Antibodies and T-Cell Hybridomas, Elsevier, N.Y., pp. 563-681), and the trioma technique, the human B-cell hybridoma technique (Kozbor et al. (1983) Immunol Today. 4: 72-79), and the EBV-hybridoma technique to produce human monoclonal antibodies (Cole et al. (1985) in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the Mabs in the invention may be cultivated in vitro or in vivo. In an additional embodiment of the invention, monoclonal antibodies can be produced in germ-free animals utilizing technology known in the art.

In general, a mouse or other appropriate host animal, such as a hamster, is immunized with the a polypeptide that includes the 13C4 epitope to induce lymphocytes that produce or are capable of producing antibodies that can specifically bind to the antigen or fragment thereof used for immunization. Alternatively, lymphocytes are immunized in vitro.

The splenocytes of the immunized host animal (e.g., a mouse) are extracted and fused with a suitable myeloma cell line using a suitable fusing agent, such as polyethylene glycol, to form a hybridoma cell (Goding (1986) Monoclonal Antibodies: Principles and Practice, pp. 59-103, Academic Press). Any suitable myeloma cell line may be employed in accordance with the present invention; however, preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

The hybridoma cells thus prepared may be seeded and grown in a suitable culture medium that preferably contains one or more substances that inhibit the growth or survival of the unfused, parental myeloma cells. The hybridoma cells obtained through such a selection and/or culture medium in which the hybridoma cells are being maintained can then be assayed to identify production of monoclonal antibodies that specifically bind the 13C4 epitope. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA) or using a Biacore. The binding affinity of the monoclonal antibody can, for example, be determined by the Scatchard analysis of Munson and Rodbard (1980) Anal Biochem. 107: 220-239.

After hybridoma cells are identified that produce antibodies of the desired specificity, affinity, and/or activity, the clones may be subcloned by limiting dilution procedures and grown by standard methods (Goding, supra). In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as *E. coli* cells, COS cells, Chinese hamster ovary (CHO) cells, or myeloma cells that do not otherwise produce immunoglobulin protein, to obtain the synthesis of monoclonal antibodies in the recombinant host cells (see e.g., Skerra et al. (1993) Curr Opin Immunol. 5: 256-262 and Pluckthun (1992) Immunol Rev. 130: 151-188).

The DNA also may be modified, for example, by substituting all or part of the coding sequence for human heavy- and light-chain constant domains in place of the homologous murine sequences (Morrison et al. (1984) Proc Natl Acad Sci. U.S.A. 81: 6851-6855), or by covalently joining to the immunoglobulin coding sequence all or part of the coding sequence for a non-immunoglobulin polypeptide. In that manner, chimeric or hybrid antibodies are prepared that have the binding specificity of an anti-13C4 epitope monoclonal antibody. Typically such non-immunoglobulin polypeptides are substituted for the constant domains of an antibody of the invention, or they are substituted for the variable domains of one antigen-combining site of an antibody of the invention to create a chimeric bivalent antibody including one antigen-combining site having specificity for the 13C4 epitope according to the invention and another antigen-combining site having specificity for a different antigen.

Modified Antibodies

Modified antibodies of the invention include, but are not limited to, chimeric monoclonal antibodies (for example, human-mouse chimeras), human monoclonal antibodies, and primatized monoclonal antibodies. A chimeric antibody is a molecule in which different portions are derived from different animal species, such as those having a human immunoglobulin constant region and a variable region derived from a murine mAb (see e.g., U.S. Pat. Nos. 4,816,567 and 4,816,397). Humanized forms of non-human (e.g., murine) antibodies are chimeric immunoglobulins, immunoglobulin chains, or fragments thereof (such as Fv, Fab, Fab', $F(ab')_2$ or other antigen-binding subsequences of antibodies) which contain minimal sequence derived from non-human immunoglobulin, such as one or more complementarity determining regions (CDRs) from the non-human species and a framework region from a human immunoglobulin molecule (see e.g., U.S. Pat. No. 5,585,089).

Humanized antibodies include human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Humanized antibodies may also include residues which are found neither in the recipient antibody nor in the imported CDR or framework sequences. In general, the humanized antibody will include substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody optimally also will include at least a portion of an immunoglobulin constant region (Fc), typically that of a human immunoglobulin.

Chimeric and humanized monoclonal antibodies can be produced by recombinant DNA techniques known in the art, for example using methods described in WO 87/02671; EP 184,187; EP 171,496; EP 173,494; WO 86/01533; U.S. Pat. No. 4,816,567; EP 125,023; Better et al. (1988) Science 240: 1041-1043; Liu et al. (1987) Proc Natl Acad Sci. U.S.A. 84: 3439-3443; Liu et al. (1987) J Immunol. 139: 3521-3526; Sun et al. (1987) Proc Natl Acad Sci. U.S.A. 84: 214-218; Nishimura et al. (1987) Cancer Res. 47: 999-1005; Wood et al. (1985) Nature 314: 446-449; Shaw et al. (1988) J Natl Cancer Inst. 80: 1553-1559; Morrison (1985) Science 229: 1202-1207; Oi et al. (1986) Biotechniques. 4: 214; U.S. Pat. No. 5,225,539; Jones et al. (1986) Nature 321: 552-525; Verhoeyan et al. (1988) Science 239: 1534; and Beidler et al. (1988) J Immunol. 141: 4053-4060. See, below for a further discussion of humanized antibodies and methods related thereto.

Another highly efficient means for generating recombinant antibodies is disclosed by Newman ((1992) Biotechnology. 10: 1455-1460); see also U.S. Pat. Nos. 5,756,096; 5,750,105; 5,693,780; 5,681,722; and 5,658,570.

Methods for humanizing non-human antibodies are well known in the art. Humanization may be essentially performed following the method of Winter and co-workers as described above (including Jones et al. (1986) Nature 321: 522-525; Riechmann et al. (1988) Nature 332: 323-327; Verhoeyen et al. (1988) Science 239: 1534-1536), by substituting rodent CDRs or CDR sequences for the corresponding sequences of a human antibody. Accordingly, such humanized antibodies are chimeric antibodies (U.S. Pat. Nos. 4,816,567 and 6,331,415). In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called best-fit method, the sequence of the variable domain of a rodent antibody is screened against the entire library of known human variable-domain sequences. The human sequence which is closest to that of the rodent is then accepted as the human framework (FR) for the humanized antibody (Sims et al. (1993) J Immunol. 151: 2296-2308; Chothia and Lesk (1987) J Mol Biol. 196: 901-917). Another method uses a particular framework derived from the consensus sequence of all human antibodies of a particular subgroup of light or heavy chains. The same framework may be used for several different humanized antibodies (Carter et al. (1992) Proc Natl Acad Sci. U.S.A. 89: 4285-4289; Presta et al. (1993) J Immunol. 151: 2623-2632.

It is also desired that antibodies be humanized with retention of high affinity for the antigen (i.e., the 13C4 epitope of Stx1) and other favorable biological properties. To achieve this goal, humanized antibodies are prepared through an analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues may be selected and combined from the consensus and import sequences so that the desired antibody characteristic, such as increased affinity for the target antigen(s), is achieved. In general, the CDR residues are directly and most substantially involved in influencing antigen binding.

Completely human antibodies are useful for therapeutic treatment of human subjects. Such antibodies may be produced, for example, using transgenic mice which are incapable of expressing endogenous immunoglobulin heavy and light chain genes, but which can express human heavy and light chain genes. The transgenic mice may be immunized in the normal fashion with a selected antigen, e.g., a polypeptide that includes the 13C4 epitope. See for examples, PCT Publication Nos. WO 94/02602, WO 00/76310; U.S. Pat. Nos. 5,545,806; 5,545,807; 5,569,825; 6,150,584; 6,512,097; and 6,657,103; Jakobovits et al. (1993) Proc Natl Acad Sci. U.S.A. 90: 2551; Jakobovits et al. (1993) Nature 362: 255-258; Bruggemann et al. (1993) Year in Immunol. 7: 33-40; Mendez et al. (1997) Nat Gene. 15: 146-156, and Green and Jakobovits (1998) J Exp Med. 188: 483-495.

Human monoclonal antibodies can also be made by the hybridoma method. Human myeloma and mouse-human heteromyeloma cell lines for the production of human monoclonal antibodies have been described, for example, by Kozbor (1984) J Immunol. 133: 3001-3005; Brodeur et al. (1987) Monoclonal Antibody Production Techniques and Applications, pp. 51-63, Marcel Dekker, Inc., New York; and Boerner et al. (1991) J Immunol. 147: 86-95.

Completely human antibodies which recognize a selected epitope can also be generated using a technique referred to as guided selection. In this approach, a selected non-human monoclonal antibody, e.g. a mouse antibody, is used to guide the selection of a completely human antibody recognizing the same epitope (Jespers et al. (1994) Biotechnology. 12: 899-903).

Examples of techniques which can be used to produce single-chain Fvs and antibodies include those described in U.S. Pat. Nos. 4,946,778 and 5,258,498; Huston et al. (1991) Meth Enzymol. 203: 46-88; Shu et al. (1993) Proc Natl Acad Sci. U.S.A. 90: 7995-7999; and Skerra et al. (1988) Science 240: 1038-1040.

Alternatively, phage display technology (McCafferty et al. (1990) Nature 348: 552-553) can be used to produce human antibodies and antibody fragments in vitro, from immunoglobulin variable (V) domain gene repertoires from non-immunized donors. Phage display can be performed in a variety of formats; see, for example, Johnson and Chiswell (1993) Curr Opin Struct Biol. 3: 564-571. Several sources of V-gene segments can be used for phage display. Clackson et al. (1991) Nature 352: 624-628 isolated a diverse array of anti-oxazolone antibodies from a small random combinatorial library of V genes derived from the spleens of immunized mice. A repertoire of V genes from non-immunized human donors can be constructed and antibodies to a diverse array of antigens (including self-antigens) can be isolated essentially following the techniques described by Marks et al. (1991) J Mol Biol. 222: 581-597, or Griffith et al. (1993) EMBO J. 12: 725-734.

The invention provides functionally-active fragments, derivatives or analogues of the immunoglobulin molecules which specifically bind to a protein that includes the 13C4 epitope. Functionally-active in this context means that the fragment, derivative or analogue is able to induce anti-anti-idiotype antibodies (i.e. tertiary antibodies) that recognize the same antigen that is recognized by the antibody from which the fragment, derivative or analogue is derived. Specifically, in a preferred embodiment, the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, $F(ab')_2$, $F(ab)_2$, Fab', Fab, and scFvs. Antibody fragments which recognize specific epitopes may be generated by known techniques, e.g., by pepsin or papain-mediated cleavage.

The invention also provides heavy chain and light chain dimers of the antibodies of the invention, or any minimal fragment thereof such as Fvs or single chain antibodies (SCAs) (e.g., as described in U.S. Pat. No. 4,946,778; Bird (1988) Science 242: 423-42; Huston et al. (1988) Proc Natl Acad Sci. U.S.A. 85: 5879-5883; and Ward et al. (1989) Nature 334: 544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al. (1988) Science 242: 1038-1041).

Alternatively, a clone encoding at least the Fab portion of the antibody may be obtained by screening Fab expression libraries (e.g., as described in Huse et al. (1989) Science 246: 1275-1281) for clones of Fab fragments that bind the specific antigen or by screening antibody libraries (see, e.g., Clackson et al. (1991) Nature 352: 624-628; Hanes and Pluckthun (1997) Proc Natl Acad Sci. U.S.A. 94: 4937-4942).

In other embodiments, the invention provides fusion proteins of the immunoglobulins of the invention, or functionally active fragments thereof. In one example, the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

In another embodiment, the invention provides for the compositions and use of pooled antibodies, antibody fragments, and the other antibody variants described herein. For example, two or more monoclonals may be pooled for use.

Therapeutic Administration

The invention also features the administration of antibodies developed using the methods above (e.g., antibodies which specifically bind the 13C4 epitope of Stx1) to subjects having, or at risk of developing a Shiga toxin associated disease.

The antibodies of the invention will be formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The therapeutically effective amount of antibody that specifically binds to the 13C4 epitope of Stx1 to be administered will be governed by such considerations, and is the minimum amount necessary to prevent, ameliorate, or treat, or stabilize, a Shiga toxin associated disease, or symptoms associated therewith. The antibody specific for the 13C4 epitope need not be, but is optionally, formulated with one or more agents currently used to prevent or treat Shiga toxin associated diseases (e.g., antibodies specific for Stx2, including 11E10 and TMA-15, or humanized or chimeric derivatives thereof). The effective amount of such other agents depends on the amount of antibody specific for the 13C4 epitope of Stx1 present in the formulation, the type of disorder or treatment, and other factors discussed above.

The antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

III. Vaccines

The invention features compositions for stimulating an immune response against the Stx1 protein.

Individuals having or at risk of developing a Shiga toxin associated disease can be treated by administration of a composition (e.g., a vaccine) containing the 13C4 epitope of the invention, where the polypeptide does not include full-length Stx1 polypeptide, preferably in an immunogenically effective amount. The peptide can be administered prophylacticly and/or therapeutically.

Different types of vaccines can be developed according to standard procedures known in the art. For example, a vaccine may be a peptide-based, nucleic acid-based, bacterial- or viral-based vaccines. A vaccine formulation containing a polypeptide or nucleic acid that encodes the polypeptide that includes the 13C4 epitope may contain a variety of other components, including stabilizers. The vaccine can also include or be co-administered with, one or more suitable adjuvants. The ratio of adjuvant to the polypeptide that includes the 13C4 epitope in the vaccine may be determined by standard methods by one skilled in the art.

In another embodiment, peptide vaccines may utilize peptides including the 13C4 epitope or functional derivatives thereof as a prophylactic or therapeutic vaccine in a number of ways, including: 1) as monomers or multimers of the same sequence, 2) combined contiguously or non-contiguously with additional sequences that may facilitate aggregation, promote presentation or processing of the epitope (e.g., class I/II targeting sequences) and/or an additional antibody, T helper or CTL epitopes to increase the immunogenicity of the 13C4 epitope, 3) chemically modified or conjugated to agents that would increase the immunogenicity or delivery of the vaccine (e.g., fatty acid or acyl chains, KLH, tetanus toxoid, or cholera toxin), 4) any combination of the above, 5) any of the above in combination with adjuvants, including but not limited to inorganic gels such as aluminium hydroxide, and water-in-oil emulsions such as incomplete Freund's adjuvant, aluminum salts, saponins or triterpenes, MPL, cholera toxin, ISCOM'S®, PROVAX®, DETOX®, SAF, Freund's adjuvant, Alum®, Saponin®, among others, and particularly those described in U.S. Pat. Nos. 5,709,860; 5,695,770; and 5,585,103; and/or delivery vehicles, including but not limited to liposomes, VPLs or virus-like particles, microemulsions, attenuated or killed bacterial and viral vectors, and degradable microspheres (see e.g., Kersten and Hirschberg (2004) Expert Rev of Vaccines. 3: 453-462; Sheikh et al. (2000) Curr Opin Mol. Ther. 2: 37-54), and 6) administered by any route or as a means to load cells with antigen ex vivo.

Dosages of a polypeptide that includes a 13C4 epitope, where the polypeptide is not full length Stx1, administered to the individual as either a prophylactic therapy or therapy against a Shiga toxin associated disease can be determined by one skilled in the art. Generally, dosages will contain between about 10 μg to 1,000 mg, preferably between about 10 mg and 500 mg, more preferably between about 30 mg and 120 mg, more preferably between about 40 mg and 70 mg, most preferably about 60 mg of the polypeptide that includes the 13C4 epitope.

At least one dose of the polypeptide that includes the 13C4 epitope will be administered to the subject, preferably at least two doses, more preferably four doses, with up to six or more total doses administered. It may be desirable to administer booster doses of the polypeptide that includes the 13C4 epitope at one or two week intervals after the last immunization, generally one booster dose containing less than, or the same amount of, the 13C4 epitope as the initial dose administered. In one example, the immunization regimen will be administered in four doses at one week intervals. Since a polypeptide or a nucleic acid may be broken down in the stomach, the immunization is preferably administered parenterally (e.g., subcutaneous, intramuscular, intravenous, or intradermal injection). The progress of immunized subjects may be followed by general medical evaluation, screening for infection by serology and/or gastroscopic examination.

IV. Examples

Figure 4:
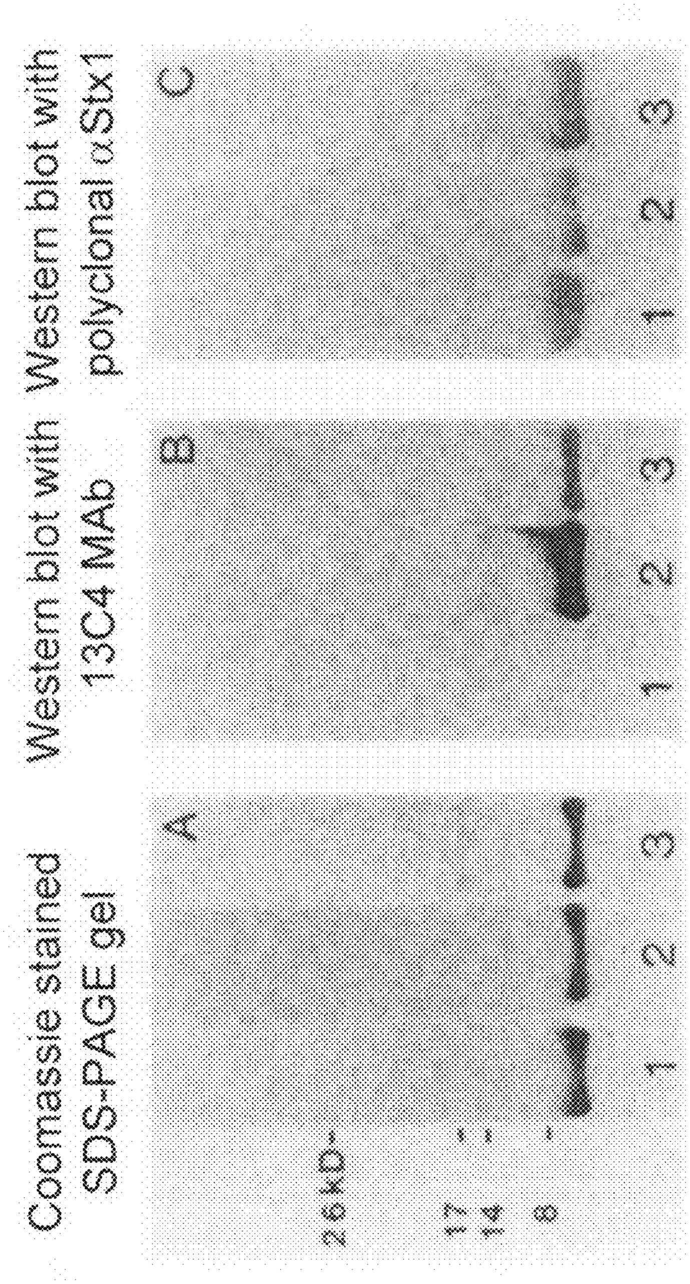
FIG. 4 shows a western blot showing Mab 13C4 recognition of the B subunit. Carboxamidomethylated B subunit (lanes 1), B subunit denatured in non reducing sample buffer (lanes 2), and B subunit denatured in the presence of β-mercaptoethanol (lanes 3) were analyzed by SDS-Page, followed by Coomassie blue staining (A) or Western blotting with Mab 13C4 (B) or with antiserum to peptide 1-25 (C) (Boyd et al. (1991) *Infect Immun.* 59:750-757)).

The murine 13C4 monoclonal antibody (MAb) binds to StxB1 and neutralizes Stx1, but does not bind to StxB2 or neutralize Stx2 despite ~73% amino acid similarity (sequences set forth in FIG. 3). It was previously shown that the 13C4 MAb epitope was a non-linear epitope that did not span any six contiguous amino acids in StxB1. Boyd et al. ((1991) *Infect. Immun.* 59:750-757) concluded that the 13C4 MAb epitope was a conformational epitope and that the disulfide bond that is formed within each Stx1B monomer is essential to generate the proper conformation that allows the 13C4 MAb to bind to Stx1 (FIG. 4). Recently, it was reported that the 13C4 MAb does not detect Stx1d, which differs from Stx1 by only three amino acids in the mature B subunit. Herein, we describe the epitope mapping of the 13C4 MAb that binds to and neutralizes Stx1.

The 13C4 MAb reacted strongly with Stx1, StxB1 and the triple-chimeric B subunit that contained all three unique regions of StxB1, but only weakly with the double-chimeric B subunit that contained the two flanking regions of StxB1; no signal was detected with the other chimeras. Mice immunized with the triple-chimeric B subunit were protected against a lethal challenge of Stx1, but not Stx2, a finding that substantiates the identified amino acids as the 13C4 epitope and indicates that incorporation of this StxB1 epitope into the Stx2 B pentamer may have masked or replaced any sites on StxB2 needed to elicit anti-Stx2 neutralizing antibodies. Because the 13C4 MAb is unable to detect Stx1d, an Stx1 variant that differs by three amino acids in the mature B subunit from Stx1, single amino acid substitutions were made in StxB1 to mimic Stx1d (T1A, G25A and N55T). The 13C4 MAb recognized StxB1 with either T1A or G25A mutations, but not the N55T mutation, a result that indicates that residue 55 is critical for the 13C4 MAb epitope. The 13C4 MAb also failed to neutralize a Stx1 holotoxin with a N55T mutation but neutralized Stx1 and Stx1 holotoxins with either T1A or G25A mutations. In conclusion, the 13C4 MAb recognizes a discontinuous or conformational epitope that spans three regions on the StxB1 monomer and requires residue 55.

Materials and Methods

Bacterial Strains, Plasmids and Media

Bacteria were grown in Luria-Bertani (LB) broth or on LB agar (Becton Dickinson and Company, Sparks, Mass.) supplemented with 100 μg/ml of ampicillin as needed for selection of recombinant plasmids.

Construction of Plasmids that Encode Chimeric $stxB_1/stxB_2$

A set of seven chimeric $stxB_1/stxB_2$ with either one, two or all three putative StxB1 regions that include the 13C4 MAb epitope were generated by a series of polymerase chain reactions (PCR) followed by splicing by overlap extension (SOE) steps. Initially, $stxB_1$ and $stxB_2$ were amplified from clones containing $stx_1$ or $stx_2$ by PCR, the $sixA_1$ and $sixA_2$ genes were removed and the $stx_1$ and $stx_2$ native promoter regions and $stxB_1$ and $stxB_2$ respectively were spliced together by SOE. These constructs were then ligated into pBluescript II $KS^-$ (Stratagene, La Jolla, Calif.). Next, the chimeric $stxB_1/stxB_2$ genes were amplified by PCR and ligated into an expression vector pTrcHis2 C (Invitrogen, Carlsbad, Calif.) and transformed into *E. coli* strain BL21 (DE3). During this round of PCR, the native $stx_1$ or $stx_2$ promoters were removed and an optimized Shine-Dalgarno sequence (TAAGGAGGACAGCTATG (SEQ ID NO: 15)) was added upstream of the translational start codons. Additionally, 18 base pairs corresponding to six histidine codons were added immediately downstream of the B genes to incorporate a common six histidine epitope on all of the B subunits. Cloning the genes for the B subunits in this manner allows for the expression of the chimeric genes to be under control of the pTrc promoter and adds a common epitope to all the constructs. This common epitope allowed for the normalization of the B subunits by performing preliminary Western blots on the same lysates and by detection with a MAb that recognizes the six histidine epitope. Three additional individual mutations were generated by SOE PCR in $stxB_1$ to mimic the three amino acid differences between the mature StxB1d and StxB1 (T1A or G25A or N55T). The constructs were sequenced at the Biomedical Instrumentation Center at the Uniformed Services University of the Health Sciences to verify that the correct mutations were generated.

Western Blotting

Purified Stx1, or whole-cell bacterial lysates expressing StxB1, StxB2 or chimeric StxB1/StxB2 his-tagged proteins were subjected to sodium dodecyl sulfate polyacrylamide gel electrophoresis (SDS-PAGE) and Western blot analysis as previously described (Smith et al. (2006) *Vaccine* 24:4122-42129). In brief, overnight cultures of *E. coli* BL21 (DE3) that contained the pTrcHis2 C-$stxB_1$ or $stxB_2$ and the seven chimeric $stxB_1/stxB_2$ clones were diluted 1:50 into 5 mL of LB broth. After 3 hours, the cultures were induced with 1 mM isopropyl β-D-thiogalactopyranoside (IPTG) and incubated for an additional 5 hours. The induced cultures were then aliquoted into microfuge tubes and SDS-PAGE sample buffer (containing 0.6 M Dithiothreitol, 10% sodium dodecyl sulfate) was added and the samples were stored at −80° C. Prior to loading onto 15% polyacrylamide gels, the samples were heated to 95° C. for 5 minutes. The concentration of wild-type or chimeric B subunits loaded was normalized on preliminary Western-blots by detection with the anti-six histidine monoclonal antibody (Novagen) and quantified using the image J program (NIH). A second Western-blot was performed using 13C4 MAb hybridoma tissue culture supernatants as the primary antibody on normalized samples. The secondary antibody for both Western-blots was goat anti-mouse immunoglobin G (IgG) conjugated to horseradish peroxidase (HRP) (Bio-Rad) at a dilution of 1:3,000. The secondary antibody was detected by chemiluminescence with the ECL-Plus Western Blotting Detection kit (Amersham Bioscience, Little Chalfont Buckhamshire, England).

Purification of the $StxB_1/StxB_2$ Triple-Chimeric B Subunit

An overnight culture of *E. coli* BL21 (DE3) that contained the pTrcHis2 C-$stxB_1/stxB_2$ triple-chimeric B subunit clone pMJS36ABC was diluted 1:50 into 3 L of LB broth. After 3 h of growth, the cultures were induced with 1 mM IPTG and incubated for an additional 5 hours. The bacteria were sedimented by centrifugation and concentrated 75-fold by resuspension in 40 ml of 50 mM phosphate buffer containing 300 mM NaCl pH 7.6 (sonication buffer). The concentrated bacterial suspensions were then disrupted by sonication, and clarified by centrifugation. The clarified lysate with the his-tagged StxB1/StxB2 triple-chimeric B subunit was then applied to a Nickel affinity column (Qiagen Inc., Valencia, Calif.), washed with sonication buffer containing 20 mM imidazole and eluted with sonication buffer containing 250 mM imidazole. The eluted proteins were dialyzed against phosphate-buffered saline, pH 7.4 (PBS) and concentrated with a Centricon 3,000 molecular weight cut off filter (Millipore corporation, Bedford, Mass.) and filtered through a 0.2 μm filter. After purification, the total protein concentration of the StxB1/StxB2 triple-chimeric B subunit preparation was 288 ng/μl, as determined by a BCA assay (Pierce). A Western blot using the 13C4 MAb and silver stained gels showed that the major purified protein was the StxB1/StxB2 triple-chimeric B subunit, although several other minor proteins were co-purified.

Mouse Immunization and Challenge

Pre-immune serum was collected from 13 CD-1 male mice that weighed 14-16 g (Charles River, Boston, Mass.). The mice were then immunized intraperitoneally (i.p.) with ~14.4 μg of the purified StxB1/StxB2 triple-chimeric B subunit in PBS mixed 1:1 with TiterMax Gold, a water-in-oil adjuvant (TiterMax USA Inc., Norcross, Ga.) (total volume 100 μl). The mice were boosted with the same amount of the purified chimeric B subunit at three week intervals, for a total of four boosts. Two weeks after the last boost, the 13 immunized mice were divided into two groups containing seven (group B) and six (group D) mice each and challenged with 10 times the 50% lethal dose ($LD_{50}$) of either Stx1 (1,250 ng) or Stx2 (10 ng) respectively. 14 non-immunized CD-1 male mice were divided into two groups containing seven mice each and challenged with 10 $LD_{50}$s of either Stx1 or Stx2, (challenge groups A and C respectively).

Enzyme-Linked Immunosorbent Assay (ELISA)

Ten days after the fourth and final boost, serum was collected form the immunized mice and the pre- and post-immunization serum from the immunized mice and serum from the 14 naive mice were used in Enzyme-linked immunosorbent assays (ELISA) to determine serum immunoglobin G (IgG) levels against StxB1 or StxB2 as reported previously (Smith et al. (2006) *Vaccine* 24:4122-42129). Briefly, 100 ng of purified Stx1 or Stx2 in PBS was used as the antigen and mouse serum was used as the primary antibody after diluting in PBS containing 0.05% Tween-20 (PBST). The secondary antibody, goat anti-mouse IgG conjugated to HRP was added at a dilution of 1:3,000 in PBST. The ELISA titers were defined as the dilution of the post-immunization serum that was +0.1 $O.D._{405}$ units above the pre-bleed values after the background was subtracted out.

In-Vitro Neutralization Assays

The pre- and post-immunization serum from the 13 immunized mice and serum from the 14 naïve mice were used in in-vitro neutralization assays against Stx1 and Stx2 as reported previously. Approximately 10 $CD_{50}$s and 25 $CD_{50}$s of purified Stx1 and Stx2 respectively were used. The actual $CD_{50}$ values were calculated retrospectively after the experiment was performed. Because the 13C4 MAb doesn't detect Stx1d, the antibody was used in neutralization assays on clarified sonic lysates of bacteria that expressed either wild-type Stx1 or Stx1 containing one of three single amino acids mutations in the B subunit (T1A or G25A or N55T). Approximately 10 $CD_{50}$s of Stx1 or Stx1 containing one of the B subunit mutations was used for these neutralization experiments. The neutralization titer was defined as the dilution of the mouse serum or 13C4 MAb that neutralized 50% of the cytotoxic effect of Stx1 or Stx2 on Vero cells. These assays were performed once in duplicate.

Eukaryotic Receptor Globotriaosyl Ceramide (Gb3) Binding Inhibition Assay.

A Gb3 binding assay was used to determine whether the 13C4 MAb could inhibit Stx1 from interacting with its receptor. In brief, 1,200 pg of purified Stx1 was diluted in PBS that contained 0.05% Tween 80 (PBST-80) and 0.1% bovine serum albumin (hereafter called binding solution), and equal volumes of Stx1 were mixed with either binding solution, undiluted 13C4 MAb (Hycult Biotechnology, Uden, The Netherlands), or serially diluted (1:4) 13C4 MAb in binding solution. The toxin-antibody mixture (total volume, 120 μl) was incubated for 2 h at 37° C. in 5% CO2, and 100 μl was then applied to Gb3 (Matreya, Inc., State College, Pa.)-coated microtiter plates (1 μg/well) that had been washed with PBST-80. The samples were incubated for 2 h at 37° C. with the primary antibody, rabbit anti-Stx1 polyclonal antibody diluted 1:5,000 in binding solution. After washing unbound primary antibody from the wells with PBST-80 and PBS, the secondary antibody, goat anti-rabbit IgG conjugated to HRP (Bio-Rad), was added at a dilution of 1:1,000 and incubated for 1 h at 37° C. After another wash with PBST-80, followed by a wash with PBS, the secondary antibody was detected with a tetramethylbenzidine peroxidase enzyme immunoassay substrate kit (Bio-Rad), and the microtiter plates were incubated at room temperature for 15 min to allow for a color change to develop. The reaction mixtures were then transferred to a fresh microtiter plate and read at 600 nm. These assays were done twice in triplicate. Controls for this experiment included incubating Stx1 with an isotype-matched irrelevant MAb (11E10; Hycult Biotechnology) or with no antibody.

Results

Figure 5:
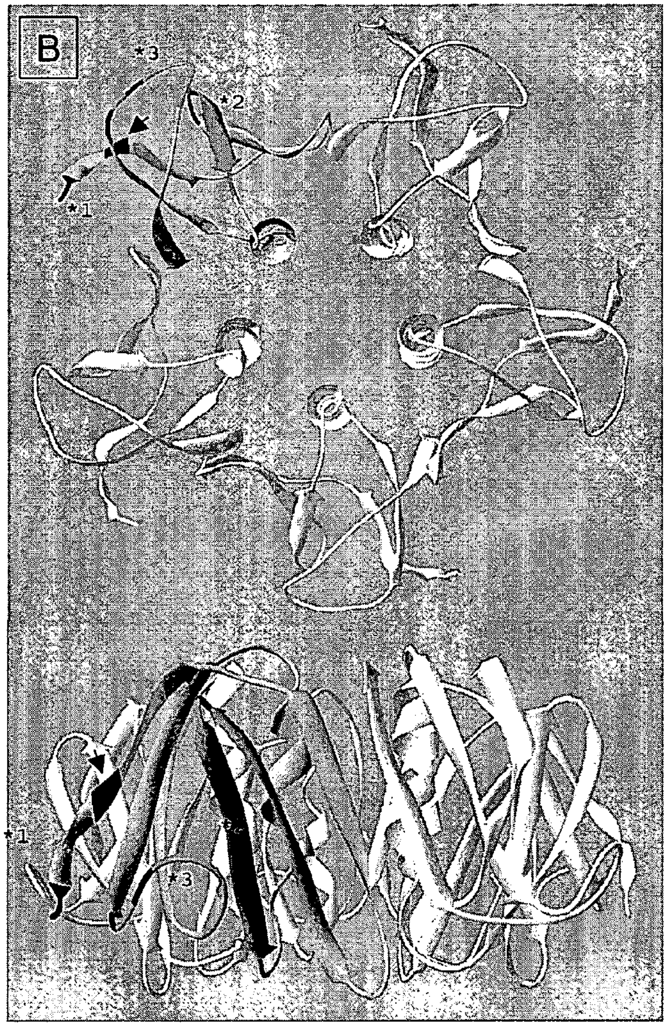
FIG. 5A shows the amino acid alignment of mature StxB2 (SEQ ID NO: 16) and StxB1 (SEQ ID NO: 17). Underlined amino acids depict non-conserved amino acids. The remaining indicated StxB1 amino acids are conserved and the dots indicate identity. The regions of sequence labeled 1, 2, and 3 correspond to SEQ ID NO: 1 (TPDCVT), SEQ ID NO: 2 (GDKELFTN), and SEQ ID NO: 3 (TNACHNGG) respectively. The three segments of the 13C4 MAb are boxed in panel A and indicated by number in FIG. 5B. These segments, when inserted into the StxB2 protein form the amino acid sequence set forth in SEQ ID NO: 4 (TPDCVTGKIEFSKYNEDDTFTVKVGDKELFTNRWNLQPLLQSAQLTGMTVTIKTNACH NGGGFAEVQFNND). The StxB2 region between SEQ ID NOs: 1 and 2 in SEQ ID NO: 4 corresponds to SEQ ID NO: 18; the StxB2 region between SEQ ID NOs: 2 and 3 in SEQ ID NO: 4 corresponds to SEQ ID NO: 19; and the StxB2 region C-terminal to SEQ ID NO: 3 in SEQ ID NO: 4 corresponds to SEQ ID NO: 20. The three amino acid differences between StxB1 and StxB1d are starred beneath the StxB1 sequence; the last star indicates the critical asparagine residue.
FIG. 5B shows the bottom and side view of the StxB pentamer crystal structure. Arrows indicate the two cysteine residues that generate the disulfide bond.

Analysis of StxB1 and StxB2 Amino Acid Alignment and Comparison of the Stx and Stx2 Crystal Structures When the amino acids of the mature StxB1 and StxB2 proteins are aligned, three regions of higher dissimilarity between the two proteins are evident (FIG. 5). Two of these regions are centered around the cysteine residues at the N and C-terminus of the protein and include amino acids 1-6 and 54-61 respectively. The third region is in the middle of StxB1, spanning amino acids 25-32. These three regions of dissimilarity were found to be located near each other on the crystal structure of StxB (StxB is identical to StxB1), illustrated on the crystal structure of the StxB pentamer in FIG. 5.

Construction of Chimeric StxB1/StxB2 Proteins

Figure 6:
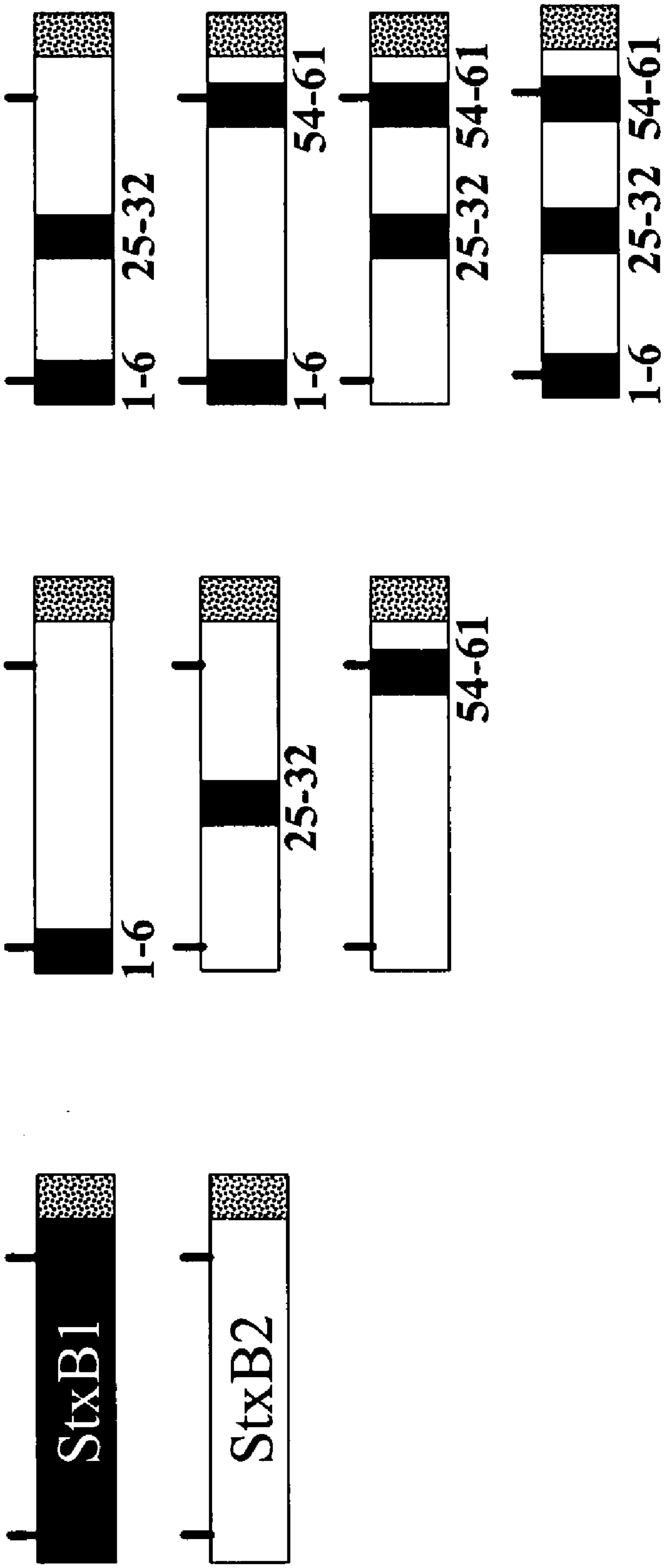
FIG. 6 shows an illustration of chimeric StxB1/StxB2 proteins. StxB1 is shown in black, Stx2 is shown in white, while the six histidine-tag is speckled. The regions of StxB1 are listed beneath the chimeric B subunits. The two cysteine residues in each B subunit are denoted by bars above the B subunits.

Wild-type StxB1 and StxB2 and seven chimeric Stx1/Stx2 B subunits consisting of one, two or all three of the unique StxB1 regions were generated by a series of PCR and splicing by over-lap extension reactions (FIG. 6). Additionally, these B subunits were his-tagged at the C-terminus to allow for normalization of the B subunits.

Figure 7:
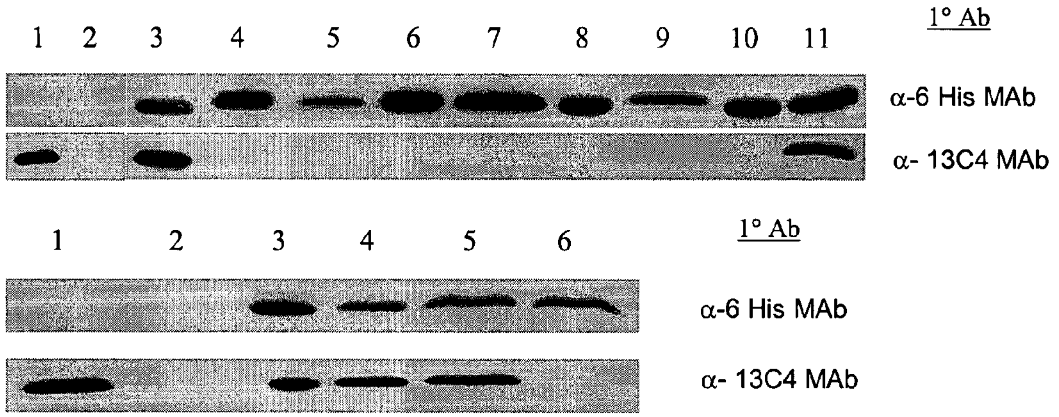
FIG. 7 shows a western blot analysis of chimeric StxB1/StxB2 proteins (top panel), and StxB1 with single amino acid mutations (bottom panel) probed with α-6 His MAb or α-13C4 MAb (bottom panel). Top panel: Lane 1, 100 ng Stx1; lane 2, vector only; lane 3, StxB1; lane 4, StxB2; lane 5, StxB1=1-6; Lane 6, StxB1=25-32; Lane 7, StxB1=54-61; Lane 8, StxB1=25-32, 54-61, lane 9, StxB1=1-6, 25-32; lane 10, StxB1=1-6, 54-61, lane 11, StxB1=1-6, 25-32, 54-61. Bottom panel: Lane 1, 100 ng Stx1; lane 2, vector only; lane 3, StxB1; lane 4, StxB1 T1A; lane 5, StxB1 G25A; Lane 6, StxB1 N55T.

Western Blot Analysis of Chimeric StxB1/StxB2 Proteins with the 13C4 Monoclonal Antibody Preliminary Western blots were performed using the Novagen α-six-histidine MAb on identical samples of whole-cell bacterial lysates containing his-tagged wild-type StxB1, StxB2 or chimeric StxB1/StxB2 proteins. The amount of B subunits in these samples was normalized using the image J program, then a second Western blot was performed using the 13C4 MAb as the primary antibody. The 13C4 MAb reacted strongly with Stx1, StxB1 and the triple-chimeric B subunit that contained all three unique regions of StxB1, but only weakly with the double-chimeric B subunit that contained the two flanking regions of StxB1; no signal was detected with the other chimeras (FIG. 7). Indicating an antibody binding site formed by regions 1-6 and 54-61 and a conformational effect on the binding site via the 25-32 region.

Analysis of StxB1 Containing Single Amino Acid Mutations by Western Blot and In-Vitro Neutralization with the 13C4 MAb.

The 13C4 MAb does not recognize Stx1d, which has only three amino acids differences in the mature B subunit from Stx1 (FIG. 8 and Bürk et al. (2003) J. Clin. Microbiol. 41: 2106-2112). Because of this, we generated three single StxB1 mutations that mimic these three differences (T1A, G25A and N5T) and probed them with the 13C4 MAb by Western blot analysis. The 13C4 MAb detected Stx1, StxB1 and StxB1 with the T1A and G25A mutations, but not the N55T mutation (FIG. 7). To further investigate the capacity of the 13C4 MAb to bind functionally to the single amino acid mutations in StxB1, in-vitro neutralizations assays were performed. A second plasmid that encoded $stxA_1$ was co-transformed into the bacteria expressing StxB1 or StxB1 with the T1A or G25A or N55T mutations such that bacteria co-transformed with these plasmids produced holotoxins. Clarified sonic lysates of bacteria forming Stx1 holotoxins were subjected to in-vitro neutralization assays with the 13C4 MAb (approximately 10 $CD_{50}$s per toxin). The 13C4 MAb neutralized the wild-type Stx1 and the Stx1 with the SxtB1 T1A and G25A mutations, but not with the N55T mutation. The fact that 13C4 does not recognize the B subunit with the single N55T mutation nor neutralize Stx1 with the N55T mutation strongly suggests that residue 55 is a critical residue for functional 13C4 binding.

Immune Response to StxB1/StxB2 Triple-Chimeric B Subunit Immunization

13 CD-1 mice were immunized with the purified triple-chimeric StxB1/StxB2 protein and boosted at three week intervals for a total of four boosts. Ten days after the final boost, post-immunization serum was collected and evaluated in ELISA and in-vitro neutralization assays and compared to the appropriate pre-immune serum and serum that was collected from the 14 non-immunized mice. The immunized mice displayed high ELISA titers to Stx1 and Stx2, 5.12 and 3.77 logs above background respectively (Table 1). None of the pre-immune serum from the 13 immunized mice or the serum from the 14 non-immunized mice displayed any appreciable ELISA titers to Stx1 or Stx2.

TABLE 1

| Stx1 ELISA titer a | Stx2 ELISA titer a | Stx1 Neutralization titer b.c | Stx2 Neutralization titer b, c |
|---|---|---|---|
| 5.12 ± 0.59 | 3.77 ± 0.43 | 2.72 ± 1.06 | 0.40 ± 0.63 |

a The geometric mean of the log IgG serum titers to Stx1 or Stx2, the error bars indicate ±1 S.D.
b The geometric mean of the log 50% neutralization titers to approximately 10 or 25 CD50s of Stx1 or Stx2 respectively, the error bars indicate ±1 S.D.
c Serum from 12 or 2 mice out of 13 neutralized Stx1 or Stx2 respectively. Samples that did not neutralize Stx1 or Stx2 were assigned a value of 0.3.

Because in-vitro neutralization titers are a better indicator of a protective immune response than are ELISA titers, in-vitro neutralization assays were performed on the serum samples against purified Stx1 or Stx2 (10 or 25 $CD_{50}$s respectively). 12 of 13 immunized mice displayed high neutralization titers to Stx1, while only two mice displayed neutralization titers to Stx2 (Table 2). The pre-immune serum from the 13 immunized mice and the serum from the 14 non-immunized mice displayed no neutralizing titers to Stx1 or Stx2. These data suggest that the regions of our chimeric B subunit that are Stx1 represent a neutralizing epitope.

TABLE 2

| Group | Mice immunized with | Mice challenged with 10 LD50 a, b of | Number of survivors/ number of mice |
|---|---|---|---|
| A | — | Stx1 | 0/7 |
| B | StxB1 = 1-6, 25-32, 54-61 | Stx1 | 6/7 |
| C | — | Stx2 | 0/7 |
| D | StxB1 = 1-6, 25-32, 54-61 | Stx2 | 1/6 |

a The LD50 was previously determined to be 125 and 1 ng/mouse for Stx1 and Stx2, respectively.
b The average weight of the mice when they were challenged was 44.9 g.

Protection of Immunized Mice Against Lethal Toxin Challenge

Two weeks after the final boost, the 13 immunized mice and the 14 control mice were challenged with either 10 $LD_{50}$ of Stx1 or Stx2. The 13 immunized mice were divided into two challenge groups, the Stx1 challenge group (group B) contained seven mice, while the Stx2 challenge group (group D) contained six mice. The 14 non-immunized mice were divided into two groups of seven and challenged with either Stx1 (group A) or Stx2 (group C). Six of the seven immunized mice survived the Stx1 challenge, while only one of six immunized mice survived the Stx2 challenge (Table 2). None of the 14 non-immunized mice survived the Stx1 or Stx2 challenge and were all dead by day four.

Gb3 Binding Inhibition Assay.

Figure 9:
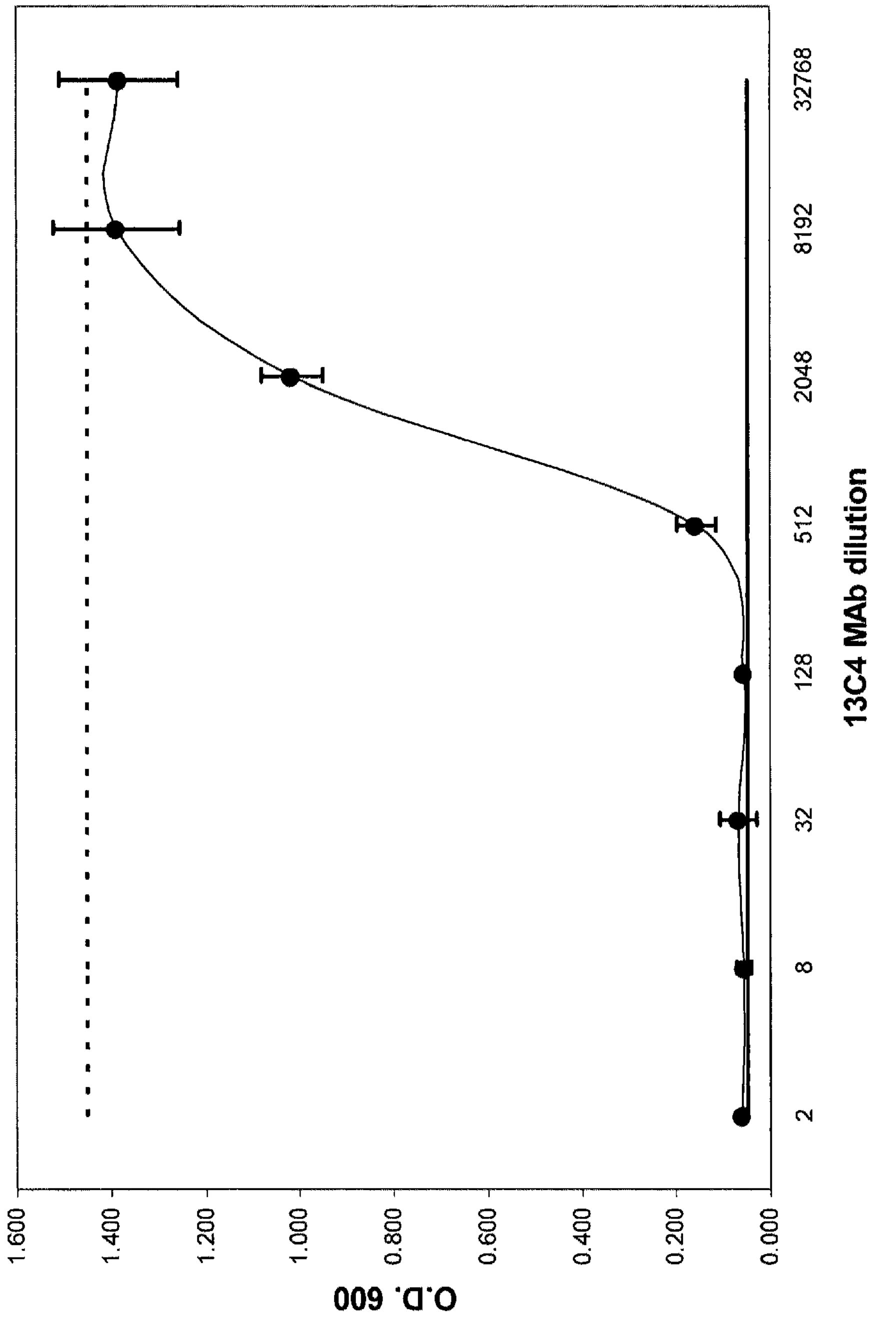
FIG. 9 is a graph showing that 13C4 MAb inhibits the binding of Stx1 to Gb3 in a dose-dependent manner. The individual circles represent averages of two experiments performed in triplicate, and the error bars indicate standard deviations (+/−1). The solid line represents the background (1 μg Gb3 plus 1,000 pg of Stx1 and secondary antibody without primary antibody), while the dashed line represents Stx1 binding without the addition of the 13C4 MAb. O.D. 600, optical density at 600 nm.

An in vitro binding inhibition assay was used to determine whether the 13C4 MAb could prevent the binding of Stx1 to Gb3. Stx1 and 13C4 MAb were incubated together and then overlaid onto Gb3-coated microtiter plates. Stx1 binding to Gb3 was not detected until the 13C4 MAb was diluted past 1:512 from a 0.1-mg/ml stock (FIG. 9). Maximal Stx1 binding occurred after the 13C4 was diluted to 1:8,000 or greater. These results show that the 13C4 Mab completely inhibited the binding of 1,000 pg of Stx1 to Gb3 in a dose-dependent manner.

Discussion

After comparing the amino acid sequences of StxB1 and StxB2, and examining the crystal structure of the StxB pentamer, we identified three nonlinear regions on StxB1 for the 13C4 MAb epitope. Western blot analysis of a series of StxB1/StxB2 chimeric proteins showed that the 13C4 MAb reacted strongly with Stx1, StxB1 and the triple-chimeric B subunit that contained all three unique regions of StxB1, but only weakly with the double-chimeric B subunit that contained the first and third regions of StxB1; no signal was detected with the other chimeras.

A set of site specific mutants showed that the 13C4 MAb specifically bound wild-type Stx1, StxB1 and StxB1 containing T1A and G25A mutations, but not StxB1 containing the N55T mutation. Furthermore, the 13C4 MAb neutralized wild-type Stx1 and Stx1 with the T1A and G25A mutations, but not the N55T mutation. Taken together, these data indicate that the asparagine at the $55^{th}$ residue of StxB1 is a critical amino acid of the 13C4 MAb epitope. The asparagine at the $55^{th}$ residue of StxB1 is also a critical amino acid for the binding of monoclonal 5-5B, another Stx1 antibody that binds the Stx1 B subunit, but fails to recognize Stx1d (Nakao et al. (2002) *Microbiol. Immunol.* 46: 777-780). Additionally, a third MAb (2H3) has been produced that recognizes StxB1, but not StxB1d, and residue 55 may play a role in that difference as well (Bürk et al. (2003) *J. Clin. Microbiol.* 41: 2106-2112). Finally, another MAb, VTm1.1 (later humanized and called TMA-15) binds to StxB2 and neutralizes Stx2 (Nakao et al. (1999) *Infect. Immun.* 67: 5717-5722, Kimura et al. (2002) *Hybrid. Hybridomics.* 21: 161-168), cannot bind to StxB2 when the $56^{th}$ amino acid is mutated (E56H). The $55^{th}$ residue of StxB1 and the $56^{th}$ residue of StxB2 are both located on the outside of the B monomers in approximately the same location. Our results and the ones outlined above, support the idea that the $55^{th}$ and $56^{th}$ amino acids of StxB1 and StxB2, respectively, are critical residues for neutralizing Mabs directed against Stx1 and Stx2.

Although the StxB1/StxB2 triple-chimeric B subunit contains mostly StxB2 (only 22 out of 71 amino acids are StxB1), higher Stx1 ELISA and neutralizations titers were achieved after immunizing with the triple-chimeric B subunit. This could be because the 22 amino acids that include the 13C4 epitope, which are on the outside of the B pentamer, are immunodominant and are good targets for neutralizing antibodies. This might explain why when the 22 amino acids including the 13C4 MAb epitope are inserted into StxB2, six of seven mice survived a lethal challenge of 10 $LD_{50}$ of Stx1, but only one of six mice survived a lethal challenge of 10 $LD_{50}$ of Stx2.

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All patents, patent applications, and publications mentioned in this specification are herein incorporated by reference to the same extent as if each independent publication was specifically and individually incorporated by reference.

What is claimed is:

1. A composition for stimulating an immune response against Stx1 comprising at least one purified polypeptide, wherein said polypeptide comprises a non-Stx1 protein scaffold and (i) SEQ ID NOs: 1, 2, and 3 or (ii) SEQ ID NOs: 1 and 3, and wherein said polypeptide has the antigenicity of Stx1, together with a pharmaceutically acceptable carrier, wherein said polypeptide does not comprise the amino acid sequence set forth in SEQ ID NO: 17 and wherein said SEQ ID NOs: 1, 2, and 3 or SEQ ID NOs: 1 and 3 are inserted into said non-Stx1 protein scaffold.

2. The composition of claim 1, wherein said scaffold comprises the amino acid sequence set forth in SEQ ID NO: 18, 19, or 20.

3. The composition of claim 1, wherein said composition does not stimulate an immune response to Stx2.

4. The composition of claim 1, wherein said polypeptide comprises an amino acid sequence at least 60 amino acids in length, wherein said amino acid sequence is at least 90% identical to the amino acid sequence set forth in SEQ ID NO: 4.

5. The composition of claim 4, wherein said polypeptide comprises the amino acid sequence set forth in SEQ ID NO: 4.

6. The composition of claim 1, wherein said composition further comprises an adjuvant.

7. A method of inducing an immune response to Stx1 in a subject, the method comprising administering the composition of claim 1 to the subject.

8. A purified polypeptide comprising a non-Stx1 protein scaffold and (i) SEQ ID NOs: 1, 2, and 3 or (ii) SEQ ID NOs: 1 and 3, wherein said polypeptide does not comprise the amino acid sequence set forth in SEQ ID NO: 17 and wherein said SEQ ID NOs: 1, 2, and 3 or SEQ ID NOs: 1 and 3 are inserted into said non-Stx1 protein scaffold and said polypeptide has the antigenicity of Stx1.

9. The polypeptide of claim 8, wherein said scaffold comprises the amino acid sequence set forth in SEQ ID NO: 18, 19, or 20.

10. A purified polypeptide comprising an amino acid sequence at least 60 amino acids in length, wherein said amino acid sequence has at least 90% sequence identity to the full length sequence of the amino acid sequence set forth in SEQ ID NO: 4, wherein said polypeptide does not comprise the amino acid sequence set forth in SEQ ID NO: 17.

11. The polypeptide of claim 10, said polypeptide comprising an amino acid sequence having at least 95% sequence identity to the full length sequence of the amino acid sequence set forth in SEQ ID NO: 4.

12. The polypeptide of claim 10, said polypeptide comprising an amino acid sequence having the full length sequence of the amino acid sequence set forth in SEQ ID NO: 4.

13. The polypeptide of claim 10, wherein said polypeptide consists of the amino acid sequence set forth in SEQ ID NO: 4.

14. A purified polypeptide comprising an amino acid sequence at least 60 amino acids in length, wherein said amino acid sequence has at least 90% sequence identity to the amino acid sequence set forth in SEQ ID NO: 4 and wherein said polypeptide is a fragment of the amino acid sequence set forth in SEQ ID NO:4, provided said fragment includes SEQ ID NOs: 1 and 3 and provided said fragment does not comprise the amino acid sequence set forth in SEQ ID NO: 17.

15. A purified polypeptide comprising an amino acid sequence at least 60 amino acids in length, wherein said amino acid sequence has at least 90% sequence identity to the amino acid sequence set forth in SEQ ID NO: 4 and wherein said polypeptide is a fragment of the amino acid sequence set forth in SEQ ID NO:4, provided said fragment includes SEQ ID NOs: 1 and 2 and provided said fragment does not comprise the amino acid sequence set forth in SEQ ID NO: 17.

16. The polypeptide of claim 14, wherein said polypeptide comprises SEQ ID NOs: 1, 2, and 3.

17. A purified polypeptide comprising an amino acid sequence at least 60 amino acids in length, wherein said amino acid sequence has at least 95% sequence identity to the amino acid sequence set forth in SEQ ID NO: 4 and wherein said polypeptide is a fragment of the amino acid sequence set forth in SEQ ID NO:4, provided said fragment includes SEQ ID NOs: 2 and 3 and provided said fragment does not comprise the amino acid sequence set forth in SEQ ID NO: 17.

18. The composition of claim 1, wherein said polypeptide comprises SEQ ID NOs: 1, 2, and 3 and a non-Stx1 protein scaffold.

19. The composition of claim 1, wherein said polypeptide comprises SEQ ID NOs: 1 and 3 and a non-Stx1 protein scaffold.

20. The purified polypeptide of claim 8, wherein said polypeptide comprises SEQ ID NOs: 1, 2, and 3 and a non-Stx1 protein scaffold.

21. The purified polypeptide of claim 8, wherein said polypeptide comprises SEQ ID NOs: 1 and 3 and a non-Stx1 protein scaffold.

22. The purified polypeptide of claim 2, wherein said scaffold comprises the amino acid sequences set forth in SEQ ID NOs: 18, 19, and 20.

23. The purified polypeptide of claim 9, wherein said scaffold comprises the amino acid sequences set forth in SEQ ID NOs: 18, 19, and 20.

* * * * *

UNITED STATES PATENT AND TRADEMARK OFFICE

CERTIFICATE OF CORRECTION

PATENT NO. : 8,293,245 B2
APPLICATION NO. : 11/788546
DATED : October 23, 2012
INVENTOR(S) : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this
Twenty-first Day of October, 2014

Michelle K. Lee
*Deputy Director of the United States Patent and Trademark Office*

SEQUENCE LISTING

```
<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Thr Pro Asp Cys Val Thr
1               5


<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Gly Asp Lys Glu Leu Phe Thr Asn
1               5


<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Thr Asn Ala Cys His Asn Gly Gly
1               5


<210> SEQ ID NO 4
<211> LENGTH: 71
<212> TYPE: PRT
<213> ORGANISM: Artificial Sequence
<220> FEATURE:
<223> OTHER INFORMATION: Synthetic

<400> SEQUENCE: 4

Thr Pro Asp Cys Val Thr Gly Lys Ile Glu Phe Ser Lys Tyr Asn Glu
1               5                   10                  15

Asp Asp Thr Phe Thr Val Lys Val Gly Asp Lys Glu Leu Phe Thr Asn
            20                  25                  30

Arg Trp Asn Leu Gln Pro Leu Leu Gln Ser Ala Gln Leu Thr Gly Met
        35                  40                  45

Thr Val Thr Ile Lys Thr Asn Ala Cys His Asn Gly Gly Gly Phe Ala
    50                  55                  60

Glu Val Gln Phe Asn Asn Asp
65                  70


<210> SEQ ID NO 5
```

<211> LENGTH: 1227
<212> TYPE: DNA
<213> ORGANISM: Shiga toxin

<400> SEQUENCE: 5

```
atgaaaataa ttatttttag agtgctaact tttttctttg ttatcttttc agttaatgtg     60
gtggcgaagg aatttacctt agacttctcg actgcaaaga cgtatgtaga ttcgctgaat    120
gtcattcgct ctgcaatagg tactccatta cagactattt catcaggagg tacgtcttta    180
ctgatgattg atagtggctc aggggataat ttgtttgcag ttgatgtcag agggatagat    240
ccagaggaag ggcggtttaa taatctacgg cttattgttg aacgaaataa tttatatgtg    300
acaggatttg ttaacaggac aaataatgtt ttttatcgct ttgctgattt ttcacatgtt    360
acctttccag gtacaacagc ggttacattg tctggtgaca gtagctatac cacgttacag    420
cgtgttgcag ggatcagtcg tacggggatg cagataaatc gccattcgtt gactacttct    480
tatctggatt taatgtcgca tagtggaacc tcactgacgc agtctgtggc aagagcgatg    540
ttacggtttg ttactgtgac agctgaagct ttacgttttc ggcaaataca gaggggattt    600
cgtacaacac tggatgatct cagtgggcgt tcttatgtaa tgactgctga agatgttgat    660
cttacattga actggggaag gttgagtagc gtcctgcctg actatcatgg acaagactct    720
gttcgtgtag gaagaatttc ttttggaagc attaatgcaa ttctgggaag cgtggcatta    780
atactgaatt gtcatcatca tgcatcgcga gttgccagaa tggcatctga tgagtttcct    840
tctatgtgtc cggcagatgg aagagtccgt gggattacgc acaataaaat attgtgggat    900
tcatccactc tgggggcaat tctgatgcgc agaactatta gcagttgagg gggtaaaatg    960
aaaaaaacat tattaatagc tgcatcgctt tcattttttt cagcaagtgc gctggcgacg   1020
cctgattgtg taactggaaa ggtggagtat acaaaatata atgatgacga tacctttaca   1080
gttaaagtgg gtgataaaga attatttacc aacagatgga atcttcagtc tcttcttctc   1140
agtgcgcaaa ttacggggat gactgtaacc attaaaacta atgcctgtca taatggaggg   1200
ggattcagcg aagttatttt tcgttga                                       1227
```

<210> SEQ ID NO 6
<211> LENGTH: 948
<212> TYPE: DNA
<213> ORGANISM: Shiga toxin

<400> SEQUENCE: 6

```
atgaaaataa ttatttttag agtgctaact tttttctttg ttatcttttc agttaatgtg     60
gtggcgaagg aatttacctt agacttctcg actgcaaaga cgtatgtaga ttcgctgaat    120
gtcattcgct ctgcaatagg tactccatta cagactattt catcaggagg tacgtcttta    180
ctgatgattg atagtggctc aggggataat ttgtttgcag ttgatgtcag agggatagat    240
ccagaggaag ggcggtttaa taatctacgg cttattgttg aacgaaataa tttatatgtg    300
acaggatttg ttaacaggac aaataatgtt ttttatcgct ttgctgattt ttcacatgtt    360
acctttccag gtacaacagc ggttacattg tctggtgaca gtagctatac cacgttacag    420
cgtgttgcag ggatcagtcg tacggggatg cagataaatc gccattcgtt gactacttct    480
tatctggatt taatgtcgca tagtggaacc tcactgacgc agtctgtggc aagagcgatg    540
ttacggtttg ttactgtgac agctgaagct ttacgttttc ggcaaataca gaggggattt    600
cgtacaacac tggatgatct cagtgggcgt tcttatgtaa tgactgctga agatgttgat    660
cttacattga actggggaag gttgagtagc gtcctgcctg actatcatgg acaagactct    720
```

-continued gttcgtgtag gaagaatttc ttttggaagc attaatgcaa ttctgggaag cgtggcatta 780
atactgaatt gtcatcatca tgcatcgcga gttgccagaa tggcatctga tgagtttcct 840
tctatgtgtc cggcagatgg aagagtccgt gggattacgc acaataaaat attgtgggat 900
tcatccactc tgggggcaat tctgatgcgc agaactatta gcagttga 948

<210> SEQ ID NO 7
<211> LENGTH: 270
<212> TYPE: DNA
<213> ORGANISM: Shiga toxin

<400> SEQUENCE: 7
atgaaaaaaa cattattaat agctgcatcg ctttcatttt tttcagcaag tgcgctggcg 60
acgcctgatt gtgtaactgg aaaggtggag tatacaaaat ataatgatga cgataccttt 120
acagttaaag tgggtgataa agaattattt accaacagat ggaatcttca gtctcttctt 180
ctcagtgcgc aaattacggg gatgactgta accattaaaa ctaatgcctg tcataatgga 240
gggggattca gcgaagttat ttttcgttga 270

<210> SEQ ID NO 8
<211> LENGTH: 315
<212> TYPE: PRT
<213> ORGANISM: Shiga toxin

<400> SEQUENCE: 8

Met Lys Ile Ile Ile Phe Arg Val Leu Thr Phe Phe Phe Val Ile Phe
1               5                   10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60

Ser Gly Ser Gly Asp Asn Leu Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly

-continued

```
                245                 250                 255

Ser Val Ala Leu Ile Leu Asn Cys His His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315


<210> SEQ ID NO 9
<211> LENGTH: 89
<212> TYPE: PRT
<213> ORGANISM: Shiga toxin

<400> SEQUENCE: 9

Met Lys Lys Thr Leu Leu Ile Ala Ala Ser Leu Ser Phe Phe Ser Ala
1               5                   10                  15

Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
        35                  40                  45

Leu Phe Thr Asn Arg Trp Asn Leu Gln Ser Leu Leu Leu Ser Ala Gln
    50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg
                85


<210> SEQ ID NO 10
<211> LENGTH: 1241
<212> TYPE: DNA
<213> ORGANISM: Shiga toxin

<400> SEQUENCE: 10

atgaagtgta tattatttaa atgggtactg tgcctgttac tgggtttttc ttcggtatcc      60

tattcccggg agtttacgat agacttttcg acccaacaaa gttatgtctc ttcgttaaat     120

agtatacgga cagagatatc gacccctctt gaacatatat ctcaggggac cacatcggtg     180

tctgttatta accacacccc accgggcagt tattttgctg tggatatacg agggcttgat     240

gtctatcagg cgcgttttga ccatcttcgt ctgattattg agcaaaataa tttatatgtg     300

gccgggttcg ttaatacggc aacaaatact ttctaccgtt tttcagattt tacacatata     360

tcagtgcccg gtgtgacaac ggtttccatg acaacggaca gcagttatac cactctgcaa     420

cgtgtcgcag cgctggaacg ttccggaatg caaatcagtc gtcactcact ggtttcatca     480

tatctggcgt taatggagtt cagtggtaat acaatgacca gagatgcatc cagagcagtt     540

ctgcgttttg tcactgtcac agcagaagcc ttacgcttca ggcagataca gagagaattt     600

cgtcaggcac tgtctgaaac tgctcctgtg tatacgatga cgccgggaga cgtggacctc     660

actctgaact gggggcgaat cagcaatgtg cttccggagt atcggggaga ggatggtgtc     720

agagtgggga gaatatcctt taataatata tcagcgatac tggggactgt ggccgttata     780

ctgaattgcc atcatcaggg ggcgcgttct gttcgcgccg tgaatgaaga gagtcaacca     840

gaatgtcaga taactggcga caggcctgtt ataaaaataa acaatacatt atgggaaagt     900

aatacagctg cagcgtttct gaacagaaag tcacagtttt tatatacaac gggtaaataa     960
```

-continued

```
aggagttaag catgaagaag atgtttatgg cggttttatt tgcattagct tctgttaatg   1020

caatggcggc ggattgtgct aaaggtaaaa ttgagttttc caagtataat gaggatgaca   1080

catttacagt gaaggttgac gggaaagaat actggaccag tcgctggaat ctgcaaccgt   1140

tactgcaaag tgctcagttg acaggaatga ctgtcacaat caaatccagt acctgtgaat   1200

caggctccgg atttgctgaa gtgcagttta ataatgactg a                       1241
```

```
<210> SEQ ID NO 11
<211> LENGTH: 960
<212> TYPE: DNA
<213> ORGANISM: Shiga toxin

<400> SEQUENCE: 11

atgaagtgta tattatttaa atgggtactg tgcctgttac tgggtttttc ttcggtatcc     60

tattcccggg agtttacgat agacttttcg acccaacaaa gttatgtctc ttcgttaaat    120

agtatacgga cagagatatc gacccctctt gaacatatat ctcaggggac cacatcggtg    180

tctgttatta accacacccc accgggcagt tattttgctg tggatatacg agggcttgat    240

gtctatcagg cgcgttttga ccatcttcgt ctgattattg agcaaaataa tttatatgtg    300

gccgggttcg ttaatacggc aacaaatact ttctaccgtt tttcagattt tacacatata    360

tcagtgcccg gtgtgacaac ggtttccatg acaacggaca gcagttatac cactctgcaa    420

cgtgtcgcag cgctggaacg ttccggaatg caaatcagtc gtcactcact ggtttcatca    480

tatctggcgt taatggagtt cagtggtaat acaatgacca gagatgcatc cagagcagtt    540

ctgcgttttg tcactgtcac agcagaagcc ttacgcttca ggcagataca gagagaattt    600

cgtcaggcac tgtctgaaac tgctcctgtg tatacgatga cgccgggaga cgtggacctc    660

actctgaact gggggcgaat cagcaatgtg cttccggagt atcggggaga ggatggtgtc    720

agagtgggga gaatatcctt taataatata tcagcgatac tggggactgt ggccgttata    780

ctgaattgcc atcatcaggg ggcgcgttct gttcgcgccg tgaatgaaga gagtcaacca    840

gaatgtcaga taactggcga caggcctgtt ataaaaataa acaatacatt atgggaaagt    900

aatacagctg cagcgtttct gaacagaaag tcacagtttt tatatacaac gggtaaataa    960
```

```
<210> SEQ ID NO 12
<211> LENGTH: 270
<212> TYPE: DNA
<213> ORGANISM: Shiga toxin

<400> SEQUENCE: 12

atgaagaaga tgtttatggc ggttttattt gcattagctt ctgttaatgc aatggcggcg     60

gattgtgcta aaggtaaaat tgagttttcc aagtataatg aggatgacac atttacagtg    120

aaggttgacg ggaaagaata ctggaccagt cgctggaatc tgcaaccgtt actgcaaagt    180

gctcagttga caggaatgac tgtcacaatc aaatccagta cctgtgaatc aggctccgga    240

tttgctgaag tgcagtttaa taatgactga                                     270
```

```
<210> SEQ ID NO 13
<211> LENGTH: 319
<212> TYPE: PRT
<213> ORGANISM: Shiga toxin

<400> SEQUENCE: 13

Met Lys Cys Ile Leu Phe Lys Trp Val Leu Cys Leu Leu Leu Gly Phe
1               5                   10                  15

Ser Ser Val Ser Tyr Ser Arg Glu Phe Thr Ile Asp Phe Ser Thr Gln
```

-continued

```
            20                  25                  30

Gln Ser Tyr Val Ser Ser Leu Asn Ser Ile Arg Thr Glu Ile Ser Thr
        35                  40                  45

Pro Leu Glu His Ile Ser Gln Gly Thr Thr Ser Val Ser Val Ile Asn
    50                  55                  60

His Thr Pro Pro Gly Ser Tyr Phe Ala Val Asp Ile Arg Gly Leu Asp
65                  70                  75                  80

Val Tyr Gln Ala Arg Phe Asp His Leu Arg Leu Ile Ile Glu Gln Asn
                85                  90                  95

Asn Leu Tyr Val Ala Gly Phe Val Asn Thr Ala Thr Asn Thr Phe Tyr
            100                 105                 110

Arg Phe Ser Asp Phe Thr His Ile Ser Val Pro Gly Val Thr Thr Val
        115                 120                 125

Ser Met Thr Thr Asp Ser Ser Tyr Thr Thr Leu Gln Arg Val Ala Ala
    130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
    210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Glu Ser Gln Pro Glu Cys Gln Ile Thr Gly Asp Arg
        275                 280                 285

Pro Val Ile Lys Ile Asn Asn Thr Leu Trp Glu Ser Asn Thr Ala Ala
    290                 295                 300

Ala Phe Leu Asn Arg Lys Ser Gln Phe Leu Tyr Thr Thr Gly Lys
305                 310                 315


<210> SEQ ID NO 14
<211> LENGTH: 89
<212> TYPE: PRT
<213> ORGANISM: Shiga toxin

<400> SEQUENCE: 14

Met Lys Lys Met Phe Met Ala Val Leu Phe Ala Leu Ala Ser Val Asn
1               5                   10                  15

Ala Met Ala Ala Asp Cys Ala Lys Gly Lys Ile Glu Phe Ser Lys Tyr
            20                  25                  30

Asn Glu Asp Asp Thr Phe Thr Val Lys Val Asp Gly Lys Glu Tyr Trp
        35                  40                  45

Thr Ser Arg Trp Asn Leu Gln Pro Leu Leu Gln Ser Ala Gln Leu Thr
    50                  55                  60

Gly Met Thr Val Thr Ile Lys Ser Ser Thr Cys Glu Ser Gly Ser Gly
65                  70                  75                  80

Phe Ala Glu Val Gln Phe Asn Asn Asp
```

85

<210> SEQ ID NO 15
<211> LENGTH: 17
<212> TYPE: DNA
<213> ORGANISM: Artificial Sequence
<220> FEATURE:
<223> OTHER INFORMATION: Synthetic

<400> SEQUENCE: 15
taaggaggac agctatg 17

<210> SEQ ID NO 16
<211> LENGTH: 70
<212> TYPE: PRT
<213> ORGANISM: Artificial Sequence
<220> FEATURE:
<223> OTHER INFORMATION: Synthetic

<400> SEQUENCE: 16

```
Ala Asp Cys Ala Lys Gly Lys Ile Glu Phe Ser Lys Tyr Asn Glu Asp
1               5                   10                  15

Asp Thr Phe Thr Val Lys Val Asp Gly Lys Glu Tyr Trp Thr Ser Arg
            20                  25                  30

Trp Asn Leu Gln Pro Leu Leu Gln Ser Ala Gln Leu Thr Gly Met Thr
        35                  40                  45

Val Thr Ile Lys Ser Ser Thr Cys Glu Ser Gly Ser Gly Phe Ala Glu
    50                  55                  60

Val Gln Phe Asn Asn Asp
65                  70
```

<210> SEQ ID NO 17
<211> LENGTH: 69
<212> TYPE: PRT
<213> ORGANISM: Artificial Sequence
<220> FEATURE:
<223> OTHER INFORMATION: Synthetic

<400> SEQUENCE: 17

```
Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Leu Ser Ala Gln Ile Thr Gly Met
        35                  40                  45

Thr Val Thr Ile Lys Thr Asn Ala Cys His Asn Gly Gly Gly Phe Ser
    50                  55                  60

Glu Val Ile Phe Arg
65
```

<210> SEQ ID NO 18
<211> LENGTH: 18
<212> TYPE: PRT
<213> ORGANISM: Artificial Sequence
<220> FEATURE:
<223> OTHER INFORMATION: Synthetic

<400> SEQUENCE: 18

```
Gly Lys Ile Glu Phe Ser Lys Tyr Asn Glu Asp Asp Thr Phe Thr Val
1               5                   10                  15

Lys Val
```

-continued

```
<210> SEQ ID NO 19
<211> LENGTH: 21
<212> TYPE: PRT
<213> ORGANISM: Artificial Sequence
<220> FEATURE:
<223> OTHER INFORMATION: Synthetic

<400> SEQUENCE: 19

Arg Trp Asn Leu Gln Pro Leu Leu Gln Ser Ala Gln Leu Thr Gly Met
1               5                   10                  15

Thr Val Thr Ile Lys
            20


<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly Phe Ala Glu Val Gln Phe Asn Asn Asp
1               5                   10
```